(12) United States Patent
Tajima et al.

(10) Patent No.: US 9,808,806 B2
(45) Date of Patent: Nov. 7, 2017

(54) SYSTEM AND METHOD FOR AUTOMATED NUCLEIC ACID AMPLIFICATION

(71) Applicant: 454 Life Sciences Corporation, Branford, CT (US)

(72) Inventors: Hideji Tajima, Matsudo (JP); Tetsuya Ueda, Matsudo (JP); Shuichi Kobayashi, Matsudo (JP); Nathan Robert Kane, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 575 days.

(21) Appl. No.: 14/467,321

(22) Filed: Aug. 25, 2014

(65) Prior Publication Data
US 2015/0056663 A1    Feb. 26, 2015

Related U.S. Application Data

(60) Provisional application No. 61/869,835, filed on Aug. 26, 2013.

(51) Int. Cl.
| | | |
|---|---|---|
| *B01L 7/00* | (2006.01) | |
| *B01F 7/00* | (2006.01) | |
| *B01F 11/00* | (2006.01) | |
| *B01L 3/00* | (2006.01) | |
| *B01F 3/08* | (2006.01) | |
| *C12Q 1/68* | (2006.01) | |
| *B01L 3/02* | (2006.01) | |
| *G01N 35/00* | (2006.01) | |

(52) U.S. Cl.
CPC .............. *B01L 7/52* (2013.01); *B01F 3/0807* (2013.01); *B01F 7/00116* (2013.01); *B01F 7/00141* (2013.01); *B01F 7/00725* (2013.01); *B01F 11/0088* (2013.01); *B01L 3/508* (2013.01); *B01L 3/0293* (2013.01); *B01L 2200/0673* (2013.01); *B01L 2300/0809* (2013.01); *B01L 2300/0858* (2013.01); *B01L 2300/1822* (2013.01); *C12Q 1/686* (2013.01); *G01N 2035/00534* (2013.01); *G01N 2035/00891* (2013.01)

(58) Field of Classification Search
None
See application file for complete search history.

(56) References Cited

U.S. PATENT DOCUMENTS

| | | | |
|---|---|---|---|
| 5,976,336 A | 11/1999 | Dubrow et al. | |
| 6,274,320 B1 | 8/2001 | Rothberg et al. | |
| 7,211,390 B2 | 5/2007 | Rothberg et al. | |
| 7,622,280 B2 | 11/2009 | Holliger et al. | |
| 7,638,276 B2 | 12/2009 | Griffiths et al. | |
| 7,842,457 B2 | 11/2010 | Berka et al. | |
| 7,927,797 B2 | 4/2011 | Nobile et al. | |
| 8,012,690 B2 | 9/2011 | Berka et al. | |
| 2004/0185484 A1 | 9/2004 | Costa | |
| 2006/0194307 A1* | 8/2006 | Yasuda | B01L 3/502761 435/288.7 |
| 2008/0277494 A1* | 11/2008 | Davies | B01F 13/0071 239/86 |
| 2009/0105959 A1 | 4/2009 | Braverman | |
| 2010/0136525 A1* | 6/2010 | Molenaar | B01L 3/5023 435/6.13 |
| 2010/0173394 A1* | 7/2010 | Colston, Jr. | B01F 3/0807 435/287.2 |
| 2010/0261229 A1* | 10/2010 | Lau | B01F 3/0807 435/91.2 |
| 2011/0003701 A1 | 1/2011 | Ferreri et al. | |
| 2011/0039303 A1* | 2/2011 | Jovanovich | B82Y 30/00 435/91.2 |
| 2011/0087016 A1 | 4/2011 | Suo | |
| 2011/0177587 A1* | 7/2011 | Nobile | B01F 3/0807 435/297.1 |
| 2011/0201526 A1 | 8/2011 | Berka | |

(Continued)

FOREIGN PATENT DOCUMENTS

| | | |
|---|---|---|
| EP | 14180909 | 2/2015 |
| WO | WO2005073410 A2 | 8/2005 |

(Continued)

OTHER PUBLICATIONS

Merrifield, R.B.: "Solid-Phase Peptide Synthesis. III. An Improved Synthesis of Bradykinin". Biochemistry (1964), vol. 3(9); 1385-1390.

Beer, Reginald N., et al., 2008, On-Chip Single-Copy Real-Time Reverse-Transcription PCR in Isolated Picoliter Droplets, Analytical Chemistry, 80(6): 1854-1858.

Kojima, Takaaki, et al., 2005, PCR Amplification from Single DNA Molecules on Magnetic Beads in Emulsion: Application for High-Throughput Screening of Transcription Factor Targets, Nucleic Acids Research, 33(17): 150.

*Primary Examiner* — Aaron Priest

(74) *Attorney, Agent, or Firm* — Cooley LLP; Ivor R. Elrifi; Christina K. Stock

(57) ABSTRACT

An embodiment of a device for automatically executing a process of generating an emulsion containing nucleic acids, amplifying the nucleic acids in the emulsion, breaking the emulsion, and separating and purifying said amplified nucleic acids, is described that comprises an emulsion generation unit for sealing beads to which nucleic acids are bound in a water-in-oil type emulsion; a nucleic acid amplification unit provided with a reaction vessel for amplifying said nucleic acids and a heating and cooling part for heating and cooling the reaction vessel; an emulsion breaking unit for breaking the emulsion after nucleic acid amplification; and a nucleic acid purification unit for recovering said amplified nucleic acids from said emulsion breaking unit.

15 Claims, 22 Drawing Sheets

(56) References Cited

U.S. PATENT DOCUMENTS

| | | | |
|---|---|---|---|
| 2012/0190032 A1* | 7/2012 | Ness | C12Q 1/6806 |
| | | | 435/6.12 |
| 2012/0236299 A1* | 9/2012 | Chiou | B01L 3/502715 |
| | | | 356/301 |
| 2012/0258516 A1* | 10/2012 | Schultz | B01F 3/0807 |
| | | | 435/194 |
| 2013/0164789 A1 | 6/2013 | Schultz et al. | |

FOREIGN PATENT DOCUMENTS

| WO | WO 2012024658 A2 * | 2/2012 | ........ B01L 3/502738 |
|---|---|---|---|
| WO | WO2012024658 A2 | 2/2012 | |

* cited by examiner (b)

(a)          (b)

SYSTEM AND METHOD FOR AUTOMATED NUCLEIC ACID AMPLIFICATION

RELATED APPLICATIONS

This application claims priority to U.S. patent application No. 61/869,835, filed Aug. 26, 2013, the contents of which is herein incorporated by reference in its entirety.

FIELD OF THE INVENTION

The present invention relates to the fields of water in oil emulsion and molecular biology. More specifically, the invention relates to systems and methods for automated emulsion generation, amplification of nucleic acids within the aqueous droplets of the emulsion, and recovery of the amplified nucleic acid products.

BACKGROUND OF THE INVENTION

The development of methods and kits for performing biological processes within the droplets of "water-in-oil" emulsions have made a tremendous contribution to the development of high throughput analysis technologies, particularly for the high throughput nucleic acid sequencing technologies that employ nucleic acid material amplified within emulsion droplets. It will be appreciated that such emulsions have been successfully employed for a number of uses that include in-vitro transcription/translation, what is referred to as directed evolution, and amplification processes. For example, each aqueous droplet of an emulsion is a micro compartment or microreactor within which the process of interest may be conducted in isolation where the many thousands of the droplets are executing the process in a massively parallel fashion. In the more specific example of nucleic acid amplification, the process can proceed with very high efficiency and without contamination from neighboring droplets. In most applications the type of amplification process performed in aqueous emulsion droplets is the well-known Polymerase Chain Reaction (PCR) method which benefits from the highly efficient heat transfer characteristics of the emulsion as well as the biological compatibility of typical water-in-oil emulsions. In addition, many emulsion embodiments for generating sequenceable material are amenable to the inclusion of solid phase substrates such as microspheres (i.e. bead type substrates) upon which the amplification products can be immobilized. This effectively sequesters the amplification products so that when the emulsions droplets are broken to recover the products each species of product can be kept separated from the others and subsequently used as a clonal population.

In general water-in-oil emulsions for use in biological contexts are disrupted or "broken" and the biological material released from the droplets is then purified for subsequent use preferably without destruction or modification of the biological integrity or composition. Traditionally, the water-in-oil emulsions have been broken using a solvent such as isopropanol and the components separated by centrifugation methods. In embodiments that employ the centrifugation method with amplified nucleic acid populations sequestered to beads it is preferable to repeat the centrifugation process several times to remove the oil and surfactants that is followed by rinsing with a buffer solution and further centrifugation the remove the isopropanol.

Traditionally, the methods for generating emulsions, amplification, and recovery of products have been manual and require substantial inputs of time and effort by users of the technology. Therefore, it is the object of the described invention to provide an efficient and automated system for generating emulsion, as well as amplifying and extracting biological elements from the emulsion without causing damage or changing the characteristics of those elements.

A number of references are cited herein, the entire disclosures of which are incorporated herein, in their entirety, by reference for all purposes. Further, none of these references, regardless of how characterized above, is admitted as prior art to the invention of the subject matter claimed herein.

SUMMARY OF THE INVENTION

Embodiments of the invention relate to the determination of the sequence of nucleic acids. More particularly, embodiments of the invention relate to reducing fluctuation in environmental conditions within a flow cell that result in the generation of undesirable detectable signal noise in semiconductor based sequencing systems.

An embodiment of a device for automatically executing a process of generating an emulsion containing nucleic acids, amplifying the nucleic acids in the emulsion, breaking the emulsion, and separating and purifying said amplified nucleic acids, is described that comprises an emulsion generation unit for sealing beads to which nucleic acids are bound in a water-in-oil type emulsion; a nucleic acid amplification unit provided with a reaction vessel for amplifying said nucleic acids and a heating and cooling part for heating and cooling the reaction vessel; an emulsion breaking unit for breaking the emulsion after nucleic acid amplification; and a nucleic acid purification unit for recovering said amplified nucleic acids from said emulsion breaking unit.

In addition, an embodiment of a method for generating an emulsion containing nucleic acids, amplifying the nucleic acids in the emulsion, breaking the emulsion, and separating and purifying said amplified nucleic acids, is described that comprises the steps of: generating an emulsion containing nucleic acids with an emulsion generation unit; transferring said emulsion from said emulsion generation unit to a nucleic acid amplification unit by means of dropping; amplifying the nucleic acids contained in said emulsion by executing heating and cooling; transferring said emulsion from said nucleic acid amplification unit to an emulsion breaking unit by means of dropping; breaking said emulsion with said emulsion breaking unit; transferring the nucleic acids contained in said broken emulsion to a nucleic acid purification unit from said emulsion breaking unit; and purifying said nucleic acids with said nucleic acid purification unit.

Further, an embodiment of a reaction vessel is described that comprises a substantially planar outer rigid frame that defines a outer perimeter of the reaction vessel comprising a first channel, a second channel, and a third channel, wherein each of the first channel, the second channel, and the third channel are operatively coupled to a tube; and a first thin film wall and a second thin film wall that define the lateral walls of the reaction vessel operatively coupled to the substantially planar outer rigid frame.

Also, an embodiment of a nucleic acid amplification unit is described that comprises a substantially planar temperature control module comprising a plurality of thermoelectric devices enabled to perform a thermocycling operation; a substantially planar back plate comprising an insulation layer and a heating element that maintains a substantially constant temperature above an ambient temperature during the thermocycling operation; and a substantially planar reaction vessel comprising an emulsion, wherein the reaction vessel is positioned between the temperature control module and the back plate.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 160 appears first in FIG. 1). All of these conventions, however, are intended to be typical or illustrative, rather than limiting.

DETAILED DESCRIPTION OF THE INVENTION

Figure 1:
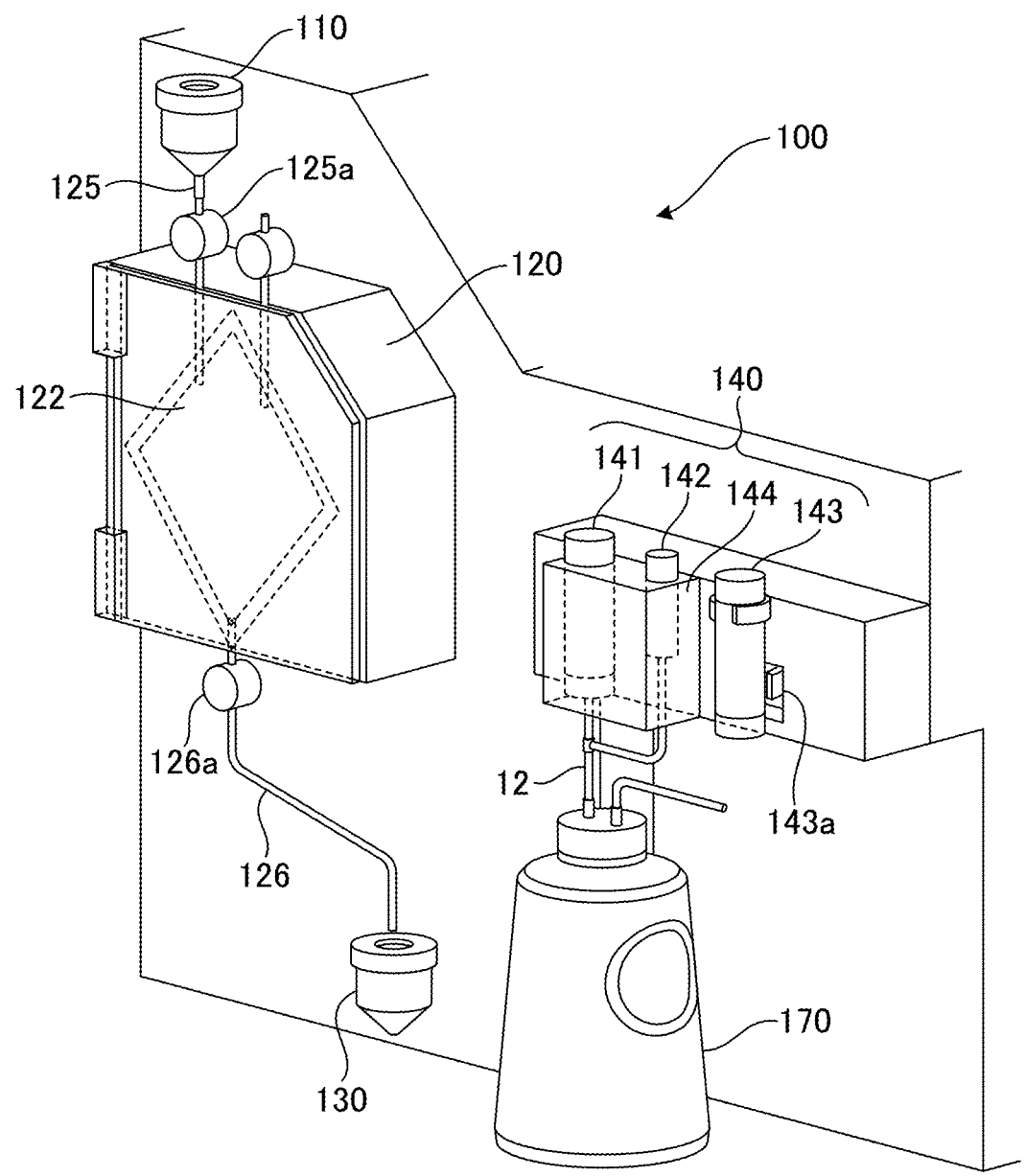
FIG. 1 is a simplified graphical representation of one embodiment of a device for generating, amplifying, and breaking emulsions.

As will be described in greater detail below, embodiments of the presently described invention include systems and methods for automatically generating an emulsion containing nucleic acids, amplifying the nucleic acids in the emulsion by PCR, breaking the emulsion, and separating and purifying the amplified nucleic acids. The described embodiments can be implemented to amplify large volumes of nucleic acids for many applications such as for use with next-generation sequencers.

a. General

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents, and other references are incorporated herein by reference. In addition, the materials, methods, and examples are illustrative only and not intended to be limiting.

The term "bead" or "bead substrate" as used herein generally refers to any type of solid phase particle of any convenient size, of irregular or regular shape and which is fabricated from any number of known materials, such as but not limited to cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase bead supports known to those of skill in the art although it will be appreciated that solid phase substrates may include a degree of porosity enabling penetration of fluids and/or biological molecule into the pores.

The term "primer" as used herein generally refers to an oligonucleotide that acts as a point of initiation of DNA synthesis under conditions in which synthesis of a primer extension product complementary to a nucleic acid strand is induced in an appropriate buffer at a suitable temperature. A primer is preferably a single stranded oligodeoxyribonucleotide.

The terms "template nucleic acid", "template molecule", "target nucleic acid", or "target molecule" generally refer to a nucleic acid molecule that is the subject of an amplification reaction.

The term "nucleotide species" as used herein generally refers to the identity of a nucleic acid monomer including purines (Adenine, Guanine) and pyrimidines (Cytosine, Uracil, Thymine) typically incorporated into a nascent nucleic acid molecule. "Natural" nucleotide species include, e.g., adenine, guanine, cytosine, uracil, and thymine. Modified versions of the above natural nucleotide species include, without limitation, alpha-thio-triphosphate derivatives (such as dATP alpha S), hypoxanthine, xanthine, 7-methylguanine, 5,6-dihydrouracil, and 5-methylcytosine.

Some or all of the described functional elements may be combined into adaptor elements that are coupled to nucleic acid templates in certain processing steps. For example, some embodiments may associate priming sequence elements or regions comprising complementary sequence composition to primer sequences employed for amplification and/or sequencing. Further, the same elements may be employed for what may be referred to as "strand selection" and immobilization of nucleic acid molecules to a solid phase substrate. In some embodiments, two sets of priming sequence regions (hereafter referred to as priming sequence A, and priming sequence B) may be employed for strand selection, where only single strands having one copy of priming sequence A and one copy of priming sequence B is selected and included as the prepared sample. In alternative embodiments, design characteristics of the adaptor elements eliminate the need for strand selection. The same priming sequence regions may be employed in methods for amplification and immobilization where, for instance, priming sequence B may be immobilized upon a solid substrate and amplified products are extended therefrom.

Additional examples of sample processing for fragmentation, strand selection, and addition of functional elements and adaptors are described in U.S. Patent Application Publication No. 2004-0185484, titled "Method for preparing single-stranded DNA libraries", filed Jan. 28, 2004; U.S. Patent Application Publication No. 2009-0105959, titled "System and Method for Identification of Individual Samples from a Multiplex Mixture", filed May 29, 2008; and U.S. Patent Application Publication No. 2011-0003701, titled "System and Method for Improved Processing of Nucleic Acids for Production of Sequencable Libraries", filed Feb. 23, 2009, each of which is hereby incorporated by reference herein in its entirety for all purposes.

Various examples of systems and methods for performing amplification of template nucleic acid molecules to generate populations of substantially identical copies are described. It will be apparent to those of ordinary skill that it is desirable in many applications in biotechnology to generate many copies of each nucleic acid element to generate a stronger signal when one or more nucleotide species is incorporated into each nascent molecule associated with a copy of the template molecule. There are many techniques known in the art for generating copies of nucleic acid molecules such as, for instance, amplification using what are referred to as bacterial vectors, "Rolling Circle" amplification (described in U.S. Pat. Nos. 6,274,320 and 7,211,390, each of which is hereby incorporated by reference herein in its entirety for all purposes) and Polymerase Chain Reaction (PCR) methods, each of the techniques are applicable for use with the presently described invention. One PCR technique that is particularly amenable to high throughput applications include what are referred to as emulsion PCR methods (also referred to as emPCR methods).

Typical embodiments of emulsion PCR methods include creating a stable emulsion of two immiscible substances creating aqueous droplets within which reactions may occur. In particular, the aqueous droplets of an emulsion amenable for use in PCR methods may include a first fluid, such as a water based fluid suspended or dispersed as droplets (also referred to as a discontinuous phase) within another fluid, such as a hydrophobic fluid (also referred to as a continuous phase) that typically includes some type of oil. Examples of oil that may be employed include, but are not limited to, mineral oils, silicone based oils, or fluorinated oils.

Further, some emulsion embodiments may employ surfactants that act to stabilize the emulsion, which may be particularly useful for specific processing methods such as PCR. Some embodiments of surfactant may include one or more of a silicone or fluorinated surfactant. For example, one or more non-ionic surfactants may be employed that include, but are not limited to, sorbitan monooleate (also referred to as Span 80), polyoxyethylenesorbitsan monooleate (also referred to as Tween 80). In the same or alternative embodiments a surfactant may include one or more of dimethicone copolyol (also referred to as Abil EM90), polysiloxane, polyalkyl polyether copolymer, polyglycerol esters, poloxamers, and PVP/hexadecane copolymers (also referred to as Unimer U-151), or a high molecular weight silicone polyether in cyclopentasiloxane (also referred to as DC 5225C available from Dow Corning).

The droplets of an emulsion may also be referred to as compartments, microcapsules, microreactors, microenvironments, or other name commonly used in the related art. The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agent may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate, such as but not limited to a bead for attachment of template and amplified copies of the template, amplified copies complementary to the template, or combination thereof. Further, the solid substrate may be enabled for attachment of other type of nucleic acids, reagents, labels, or other molecules of interest.

In many embodiments where water-in-oil emulsions employed in biological contexts, the droplets of the emulsion need to be disrupted or "broken" to release the biological material from the droplets that is subsequently purified, preferably without destruction or modification of the biological integrity or composition. Traditionally, the water-in-oil emulsions have been broken using an organic solvent such as isopropanol and the components separated by centrifugation methods. In embodiments that employ the centrifugation method with amplified nucleic acid populations sequestered to beads, it is preferable to repeat the centrifugation process several times to remove the oil and surfactants, followed by rinsing with a buffer solution and further centrifugation the remove the isopropanol. Alternatively in some embodiments the aqueous phase (or non-aqueous phase) comprising the biological material of interest can be recovered from an emulsion system broken using what is referred to as a "salting out" effect after the emulsion has been broken with isopropanol or other organic solvent. The salting out embodiments are automatable and offer substantial processing improvements over traditional methods because they are highly efficient, maintain biological integrity, and are amenable for execution by automated/robotic type platforms. Additional examples of breaking emulsions and isolation of materials are described in US Patent Application Publication No 2011-0087016, which is hereby incorporated by reference herein in its entirety for all purposes After emulsion breaking and bead recovery, it may also be desirable in typical embodiments to "enrich" for solid substrates such as beads having a successfully amplified population of substantially identical copies of a template nucleic acid molecule immobilized thereon. For example, a process for enriching for "DNA positive" beads may include hybridizing a primer species to a region on the free ends of the immobilized amplified copies, typically found in an adaptor sequence, extending the primer using a polymerase mediated extension reaction, and binding the primer to an enrichment substrate such as a magnetic or sepharose bead. It will also be appreciated by those of ordinary skill that the primer species may first be immobilized on the enrichment substrate prior to hybridization. A selective condition may be applied to the solution comprising the beads, such as a magnetic field or centrifugation, where the enrichment bead is responsive to the selective condition and is separated from the "DNA negative" beads (i.e., no or few immobilized copies).

Embodiments of an emulsion useful with the presently described invention may include a very high density of droplets or microcapsules enabling the described chemical reactions to be performed in a massively parallel way. Additional examples of emulsions employed for amplification and their uses for applications such as sequencing are described in U.S. Pat. Nos. 7,638,276; 7,622,280; 7,842,457; 7,927,797; and 8,012,690 and U.S. Patent Application Publication No. 2011-0201526, each of which is hereby incorporated by reference herein in its entirety for all purposes.

Also, the systems and methods of the presently described embodiments of the invention may include implementation of some design, analysis, or other operation using a computer readable medium stored for execution on a computer system.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell", such as but not limited to Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows-type operating system (such as Windows XP, Windows Vista, or Windows 7) from the Microsoft Corporation; the Mac OS X operating system from Apple Computer Corp. (such as Mac OS X v10.6 "Snow Leopard" operating systems); a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also, a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example, some commonly employed web browsers include Microsoft Internet Explorer 8 available from Microsoft Corporation, Mozilla Firefox 3.6 from the Mozilla Corporation, Safari 4 from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

b. Embodiments of the Presently Described Invention

As described above, the disclosure relates to a systems and methods comprising for automatically generating an emulsion containing nucleic acids, amplifying the nucleic acids in the emulsion by PCR, breaking the emulsion, and separating and purifying the amplified nucleic acids. Embodiments of the presently described invention can amplify large volumes of nucleic acids without the requirement of frequent user intervention that can be applied various technologies such as to high throughput sequencing technologies. For example, embodiments of the invention removes the need for one or more technicians to manually interact and perform individual steps making it possible to easily and efficiently execute the preparation of nucleic acids, emulsion generation, nucleic acid amplification, and purification single-handedly by automation. Importantly the result makes it possible to avoid the troublesomeness of user operations and to increase operational efficiency.

By way of example, in some embodiments of a manual emulsion generation process, a water-in-oil type emulsion is created by mechanical agitation such as by stirring an aqueous solution that includes beads typically comprising an immobilized primer species to which nucleic acid samples are bound, PCR reagents (polymerases, primers, PCR buffers, and the like), and a hydrophobic solvent such as an oil in a container. In the present example, the creation of an emulsion may be accomplished by stirring, vortexing, or other mechanical agitation means known to those of ordinary skill in the related art where a discrete discontinuous phase comprising droplets and continuous phase is formed from a combined mixture of oil and aqueous solution.

Next, the generated emulsion may be subjected to an amplification process by PCR (emulsion PCR) or isothermal amplification process. For PCR applications, amplification can be performed by a thermal cycler in a reaction solution at a milliliter level such as a solution with a large volume of 5 to 40 ml. After PCR, breaking of the emulsion is performed with a breaking solution such as isopropanol, and the amplified solution is washed. After washing, an enrichment procedure is employed to select beads to which the amplified nucleic acids are bonded and immobilized, and in some cases the target nucleic acids are purified. The enrichment procedure typically employs embodiments of enrichment bead that include polystyrene (for use in a glycerol gradient) or magnetic beads, where the enrichment bead may be coated with a primer species complementary to a region on the amplified population for this selection.

In some embodiments of the presently described invention, the respective containers for performing the basic emulsion generation process, the nucleic acid amplification process, and the emulsion breaking process described above may be made independent.

In the same or alternative embodiments of the presently described invention, some or all of the respective containers for performing the basic three processes described above may be connected by liquid transfer channels that enable liquid transfer by means of head drop (i.e. gravity), and liquids can be transferred through the head drop of three levels managed by the opening and closing of valves or other embodiments of channel opening and closing devices. The term "head drop" as used herein generally refers to the force and pressure of a fluid created by gravity that pulls fluids downward and is a function of the height differential and the specific gravity of a fluid. For example, channel opening and closing devices include members in which channels can be opened and closed by a mechanical control part such as pinchcock clamps, solenoid valves, or the like. Also, the liquid transfer channels can be formed as soft (flexible) tubes or hoses, or created by attaching two soft films to one another so as to form long, thin spaces between the two films. Making the liquid transfer channels soft makes it possible to attach pinchcock clamps or the like as channel opening and closing devices at arbitrary positions of the liquid transfer channels. Further, a soft fluorine resin, soft vinyl chloride, silicon rubber, or the like, for example, can be used as the soft material used for the liquid transfer channels. In the described embodiments each of the processes can be performed fully automatically.

Device

An embodiment of the device for implementing the processes described above is shown in FIG. 1. FIG. 1 illustrates an embodiment of device 100 of the presently described invention that comprises emulsion generation unit 110, nucleic acid amplification unit 120 that includes reaction vessel 122 for nucleic acid amplification and a thermal cycler (i.e. a Peltier device). Device 100 also comprise emulsion breaking unit 130 for breaking the emulsion after nucleic acid amplification, and nucleic acid purification unit 140 for recovering the amplified nucleic acids.

(1) Emulsion Generation Unit

Emulsion generation unit 110 comprises a container into which components are added for encapsulation in aqueous droplets of a water-in-oil type emulsion. Typically the components comprise nucleic acid template molecules, bead substrates, and nucleic acid amplification reagents. Other components for the continuous oil phase may also include hydrophobic oil, surfactants, and the like. In the described embodiments, emulsion generation unit 110 may form a water-in-oil type emulsion by spinning or oscillating a stirring rod with a paddle or blade structure positioned within unit 110 at a desired rate to create shear forces and produce aqueous droplets of a desired dimension. For example, emulsion generation unit 110 produces hydrophilic microscopic water droplets containing single beads encapsulated in micelles surrounded by a hydrophobic liquid. In the present example the material of the beads comprises a polymer such as polystyrene and may comprise a diameter selected in accordance with the application used such as beads within a range of 1.5 µm to 20 µm.

The emulsion generated by the emulsion generation unit 110 is transferred by head drop via liquid transfer channel 125 (tube, hose, or the like) to reaction vessel 122 for execution of a nucleic acid amplification process by nucleic acid amplification unit 120. In the described embodiment, the container of the emulsion generation unit 110 and the liquid transfer channel 125, connected to the bottom end thereof, may be molded integrally.

Figure 2:
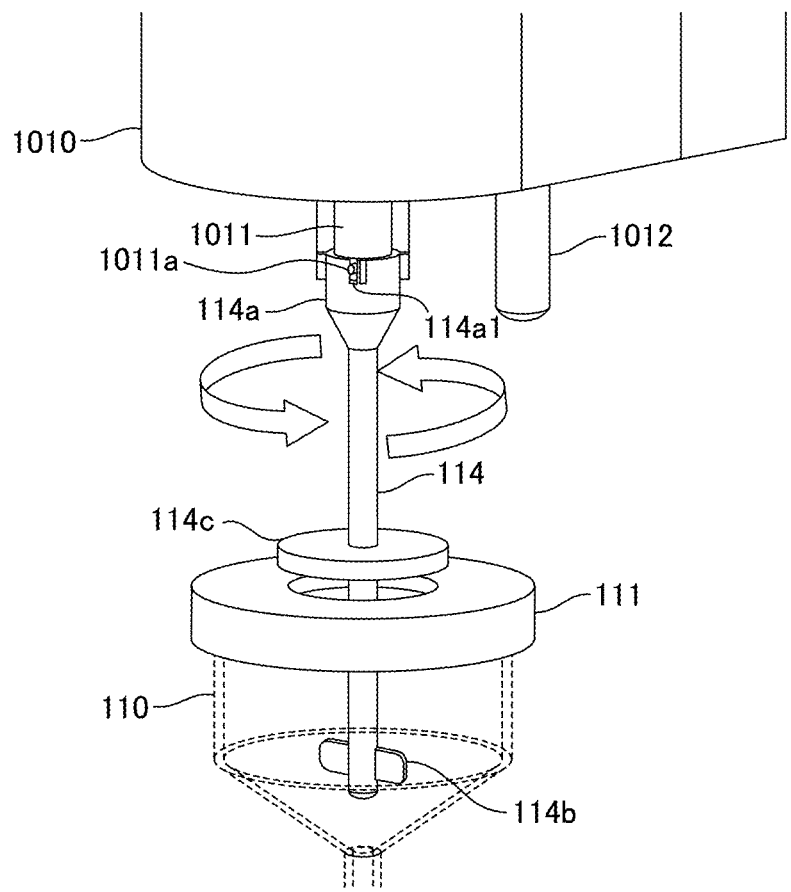
FIG. 2 is a simplified graphical representation of one embodiment of an emulsion generation unit.
Figure 3:
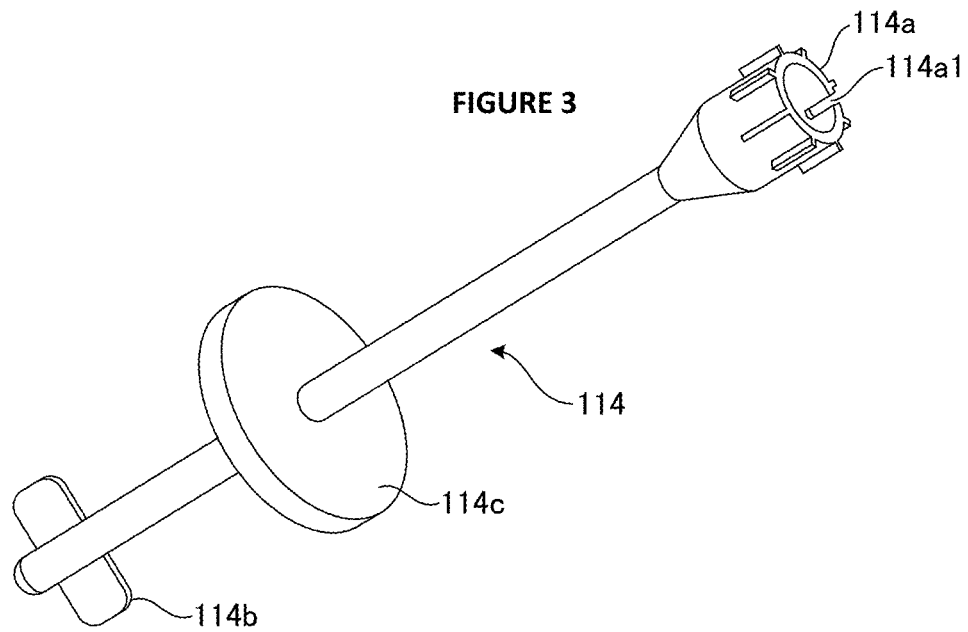
FIG. 3 is a simplified graphical representation of one embodiment of a stirring rod used in the emulsion generation unit of FIG. 2.

FIG. 2 is an illustration of an embodiment of emulsion generation unit 110 with an embodiment of stirring rod 114 comprising blade structures, where stirring rod 114 detachably couples to stirring rod connection part 1011 on nozzle unit 1010. As shown in FIG. 3, stirring rod 114 comprises connection end part 114a constructed and arranged to couple to stirring rod connection part 1011 and stirring end part 114b having blades for mechanically agitating a fluid mixture.

A rotational misalignment prevention mechanism for preventing the misalignment or sticking of the stirring rod while rotating or oscillating is provided at the connection part of stirring rod connection part 1011 and stirring rod 114. The rotational misalignment prevention mechanism comprises notch part 114a1 formed in the connection end part 114a of the stirring rod 114 and a protruding part 1011a formed on connection part 1011. In the described embodiments, protruding part 1011a is inserted into notch 114a1. It will also be appreciated that in some embodiments a protruding part may also be formed in the connection end part 114a, and a notch part may be formed in the stirring rod connection part 1011. Stirring rod 114 may also be provided with a disc-shaped liquid anti-splash part 114c in the axial central region thereof. Liquid anti-splash part 114c prevents fluids from splashing to the outside of the unit when generating the emulsion with the stirring rod 114 inside the emulsion generation unit 110 or the like.

Figure 17:
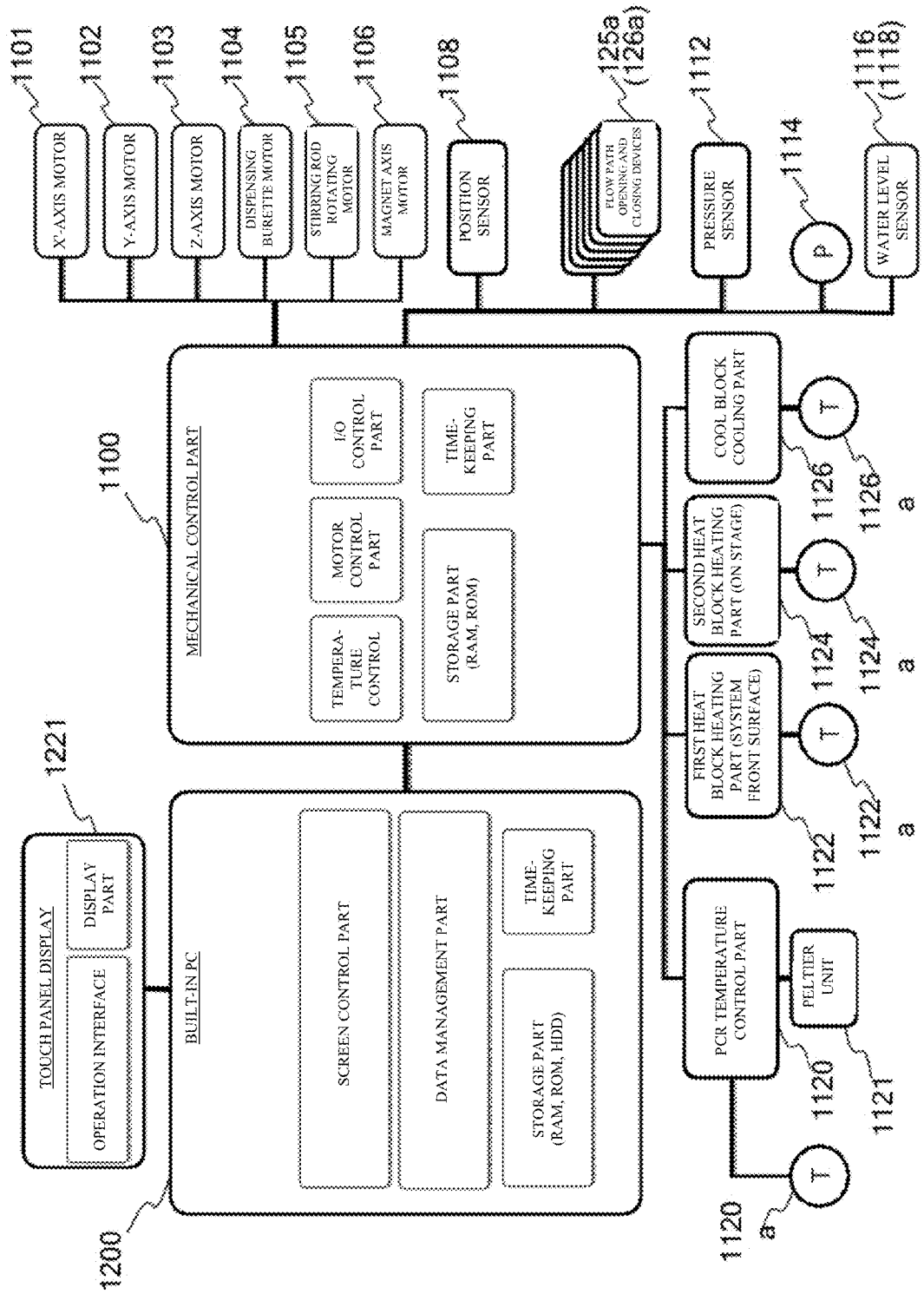
FIG. 17 is a simplified graphical representation of one embodiment of the configuration of the control part of the nucleic acid amplification automation system.

Stirring rod connection part 1011 of the nozzle unit 1010 can be rotated at a prescribed revolution speed or oscillated at a desired frequency by a stirring rod rotating motor 1105 (FIG. 17). For example, the rotational direction is such that the device is rotated 360 degrees in one direction, but the device may be oscillated by rotating in forward and reverse directions within a prescribed range such as 90 degrees and frequency. Accordingly, as shown in FIG. 2, when connection end part 114a of stirring rod 114 is connected to stirring rod connection part 1011 of nozzle unit 1010 and stirring end part 114b of stirring rod 114 is moved within the emulsion generation unit 110 so as to rotate or oscillate stirring rod 114, the fluid mixture inside emulsion generation unit 110 is mechanically agitated by the stirring end part 114b that produces shear forces in the fluid mixture that results in the generation of an emulsion.

In FIG. 2, one opening may be formed in an upper lid 111 of the emulsion generation unit 110 so that reagents may be aspirated and discharged from the opening by a dispensing burette 1012. Further, stirring rod 114 may be inserted into the emulsion generation unit 110 through this opening to enable stirring. A disposable dispensing tip may be mounted on the dispensing burette 1012.

Figure 4A:
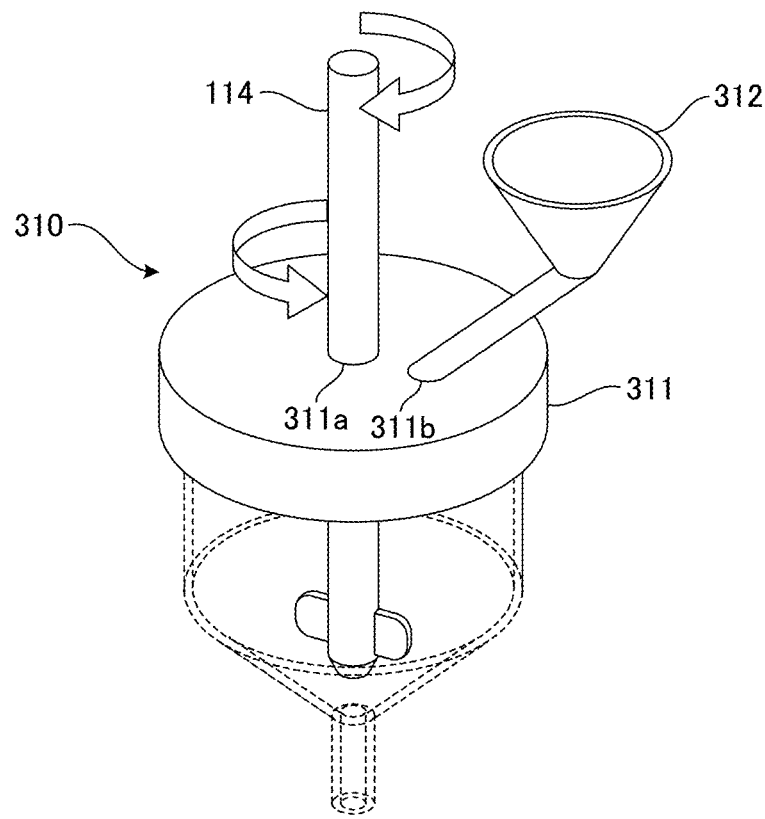
FIGS. 4A and 4B are simplified graphical representations of an alternative embodiment of an emulsion generation unit.
Figure 4B:
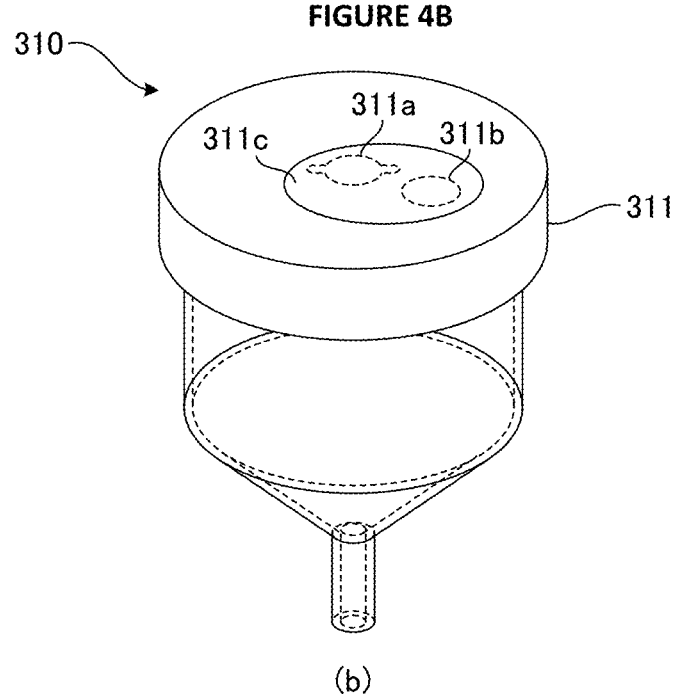

As illustrated in FIGS. 4A and B, emulsion generation unit 310 serves as an alternative embodiment to the emulsion generation unit 110 shown in FIG. 2. In this alternative embodiment, an opening for the stirring rod and an opening for the dispensing burette are respectively provided instead of a single opening. In the example illustrated in FIG. 4A, emulsion generation unit 310 comprises an embodiment of stirring rod 114 which is inserted through a first opening part 311a of an upper lid 311 and a funnel-shaped injection port 312 connected to a second opening part 311b in the upper surface. For example, reagents may be injected into the injection port 312 via a dispensing burette and stirring rod 114 can be rotated at or oscillated as described previously by stirring rod rotating motor 1105. FIG. 4B illustrates an embodiment where first and second opening parts 311a and 311b are covered with an aluminum seal 311c or the like before stirring rod 114 or injection port 312 is attached to the upper lid 311. For example, the lower end part of stirring rod 114 or injection port 312 is enabled to penetrate aluminum seal 311c in order to access the interior of emulsion generation unit 310.

(2) Nucleic Acid Amplification Unit

Figure 5:
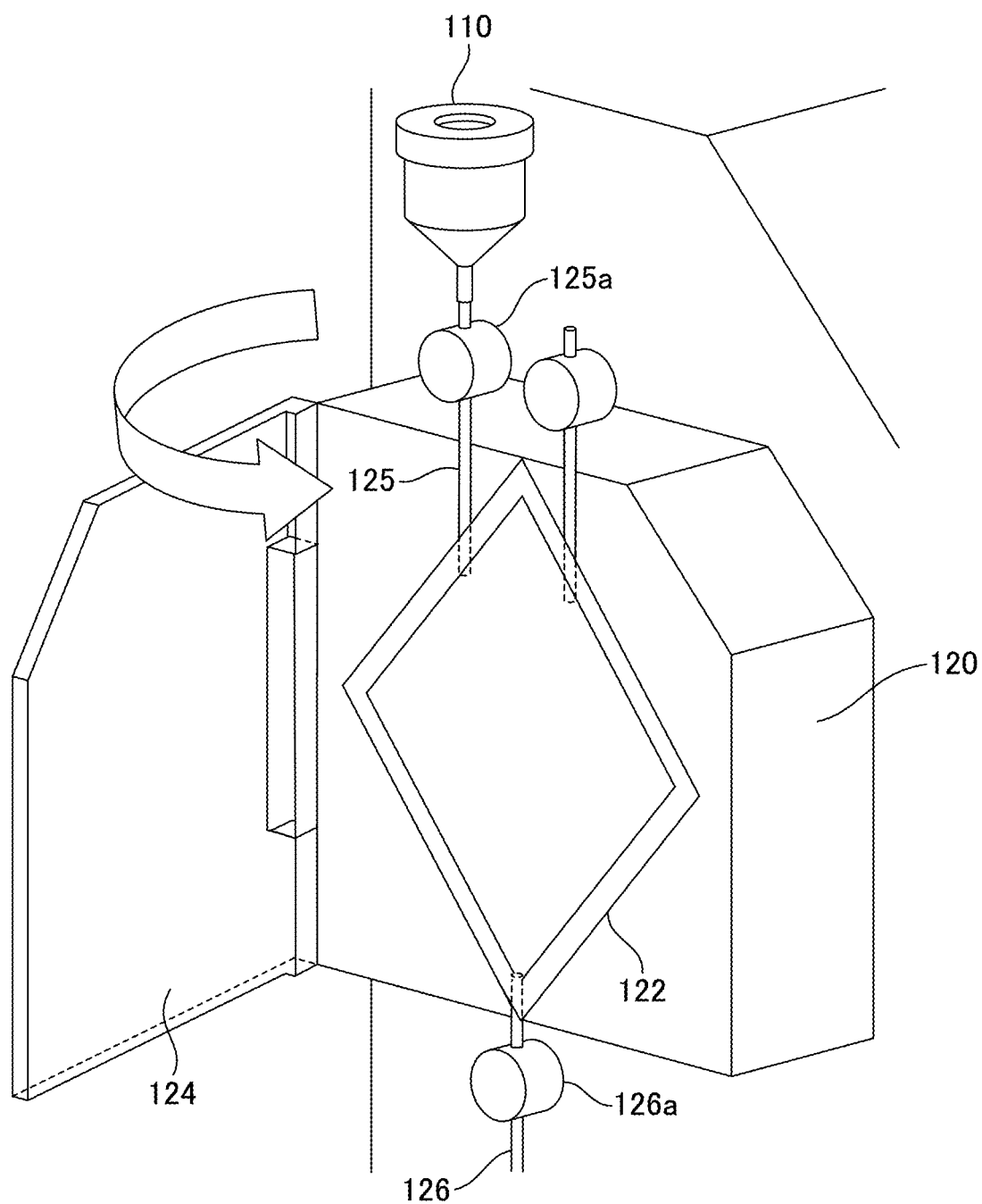
FIG. 5 is a simplified graphical representation of one embodiment of a nucleic acid amplification unit.

FIG. 5 provides an illustrative example of one embodiment of a unit for amplifying nucleic acids in an emulsion by PCR or the like. Nucleic acid amplification unit 120 as illustrated in FIG. 5 comprises a bag-like reaction vessel 122 having a reaction space formed between thin layers of material arranged in a parallel planar relationship that allow for efficient thermal transfer and define a chamber where an entire volume of fluid is in close contact to a temperature control device such as a thermoelectric Peltier device (not shown). In the described embodiments the temperature control device is operably coupled to the back surface of reaction vessel 122 and is capable of uniformly heating and cooling the volume of fluid within the chamber of reaction vessel 122. It is also desirable in the described embodiments to provide at least one heat-insulating cover 124 which can be freely opened and closed over the opening part of nucleic acid amplification unit 120. Further, liquid transfer channel 125 for liquid transfer by means of head drop is provided between the lower part of the container of emulsion generation unit 110 and the upper part of nucleic acid amplification unit 120. Channel opening and closing device 125a is provided on the liquid transfer channel 125 to control the flow of fluid into reaction vessel 122. For example, when channel opening and closing device 125a is opened after an emulsion solution is generated by emulsion generation unit 110, the emulsion solution can be transferred by means of gravity flow into reaction vessel 122 of nucleic acid amplification unit 120 via the liquid transfer channel 125. In the present example, a claw-shaped member which blocks the soft liquid transfer channel when pressed may be used as channel opening and closing device 125a.

Next, nucleic acid amplification unit 120 executes a thermal cycling program for PCR amplification. For example, the emulsion transferred into reaction vessel 122 is a water-in-oil type emulsion comprising aqueous compartments, a plurality of which comprise a single nucleic acid template, a bead to which amplified copies of nucleic acid template may be bound, nucleic acid amplification reagents such as primers, DNA polymerases, and deoxynucleotide triphosphates. In the present example, adaptors have been added to the ends of the nucleic acid template molecules that include primer sites recognized by the amplification primers in the compartments as described above. The thermal cycling program defines the thermal reaction conditions for PCR amplification and may be modified based on a number of parameters as is generally appreciated by those of ordinary skill in the art. In the present example, an initial reaction step may be performed for 1 to 3 minutes at 94° C., (however, this reaction step is arbitrary); next a denaturing step of 30 seconds to 1 minute at 94° C.; followed by an annealing step for 30 seconds to 1 minute at 40 to 60° C. The denaturing and annealing steps are repeated for a prescribed number of cycles, each cycle consisting of a 1- to 3-minute expansion reaction within a temperature range at which a polymerase reaction is possible without the primer being separated from the nucleic acids (for example, approximately 72° C.). The emulsion may also be heated once again for 5 to 10 minutes at 72° C. after the prescribed numbers have been completed as a post amplification step.

(3) Emulsion Breaking Unit

Emulsion breaking unit 130 performs steps for breaking the emulsion containing the nucleic acids amplified by nucleic acid amplification unit 120. As illustrated in FIG. 1, emulsion breaking unit 130 is disposed below nucleic acid amplification unit 120. Further, liquid transfer channel 126 connects the lower part of reaction vessel 122 and the opening in the upper part of emulsion breaking unit 130 for liquid transfer by means of head drop. Also, channel opening and closing device 126a is provided on liquid transfer channel 126. For example, when channel opening and closing device 126a is opened after the nucleic acids are amplified by the nucleic acid amplification unit 120, the emulsion containing the amplified nucleic acids can be transferred by means of gravity flow into the emulsion breaking unit 130 via liquid transfer channel 126. In the present example, emulsion breaking unit 130 adds an alcohol to the emulsion that disrupts the aqueous microreactors and releases the contents into a complex mixture. In the present example, the breaking is aided by stirring using a stirring rod (not shown) and subsequently the oil content formed in the emulsion is removed from the solution using a salt out method as described above or other method generally known in the art.

(4) Nucleic Acid Purification Unit (Bead Classification and Recovery Unit)

Figure 6:
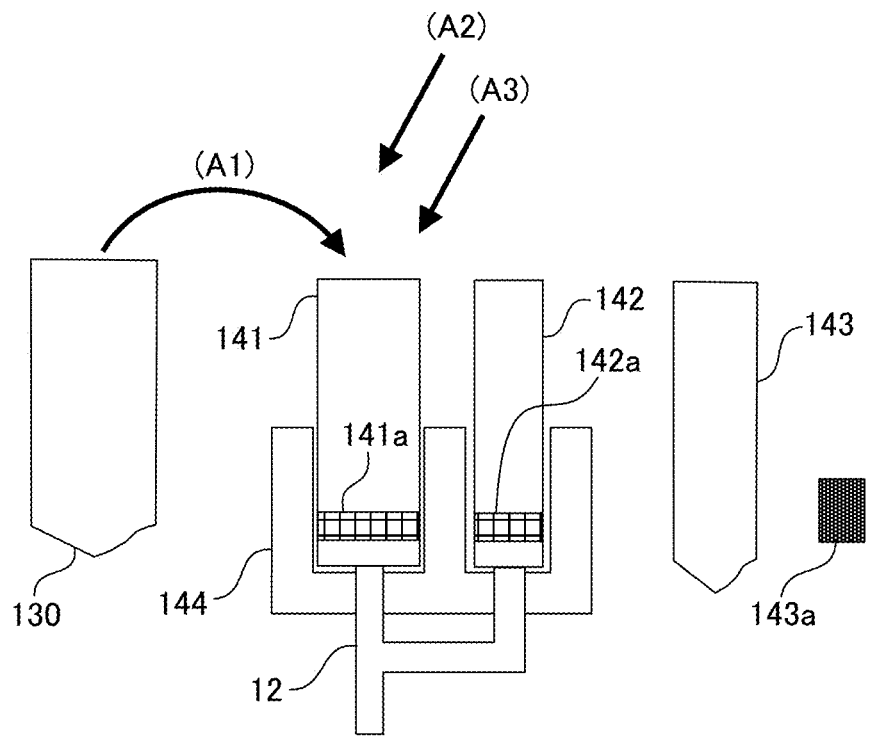
FIG. 6 is a simplified graphical representation of one embodiment of the processing of the nucleic acid purification unit.

As shown in FIG. 1, nucleic acid purification unit 140 comprises first tube 141, second tube 142, and third tube 143. FIG. 6 further illustrates, first tube 141 and second tube 142 respectively have a first filter 141a and a second filter 142a. Vacuum trap 170 is connected below the first filter 141a of the first tube 141 and the second filter 142a of the second tube 142, and vacuum trap 170 is decompressed by a vacuum pump not shown in the drawings. Further, heat block 144 is disposed around the first tube 141 and the second tube 142 so as to enable the heating of the first tube 141 and the second tube 142. A magnet 143a is disposed on the outside surface of the third tube 143, and this magnet 143a can be used to adsorb magnetic beads in the solution from the broken emulsion and purify the amplified nucleic acids bound to beads. For example, magnet 143a can move between an adsorption position near the third tube 143 for adsorbing the magnetic beads and a separation position at a distance from third tube 143 where the magnetic beads are not adsorbed. The details of the nucleic acid purification process using magnetic beads will be given below.

(4-1) Principle of Bead Classification and Recovery

A general description of embodiments of the principle of the bead classification and recovery method executed by nucleic acid purification unit 140 will be described hereinafter.

In the described embodiments, nucleic acids such as DNA amplified by PCR are bound to beads, but null beads to which no amplified nucleic acids are bound are also contained in the solution from the broken emulsion. For example, after breaking the emulsion, double-stranded DNA immobilized on the beads is denatured by melt-solution (for example, the addition of a 100 to 150 mM (molar concentration) sodium hydroxide solution) to release free single-stranded DNA from the beads into solution and leaving single stranded DNA immobilized on the beads. Next, a biotin-modified enriching primer (primer that may be attached to streptavidin coated magnetic beads by a biotin disposed on the ends of the primers) is annealed to the single-stranded DNA on the nucleic acid-bound beads and in some embodiments extended by a polymerase to increase the strength of the binding (typically to a primer site in an adaptor region that is part of the amplified nucleic acid population is complementary to the enriching primer). It will be appreciated that the enriching primer may be attached to the magnetic bead before or after annealing to the single stranded DNA. As a result, the nucleic acid-bound and the magnetic beads (also referred to as enrichment beads) are bound via the annealed primer. In the presently described example, the magnetic beads comprise magnetic or paramagnetic material and are prepared by using streptavidin to coat beads. Since the nucleic acid-bound beads are bound to the magnetic beads, only the nucleic acid-bound beads and the magnetic beads are adsorbed by the magnet. The beads that do not have bound nucleic acid are washed away and the nucleic acid-bound beads are exposed to a melt-solution that causes the annealed primer (and extended product) to separate from the amplified nucleic acids and thus separation from the magnetic beads.

(4-2) Example of Bead Classification and Recovery Method

Figure 15:
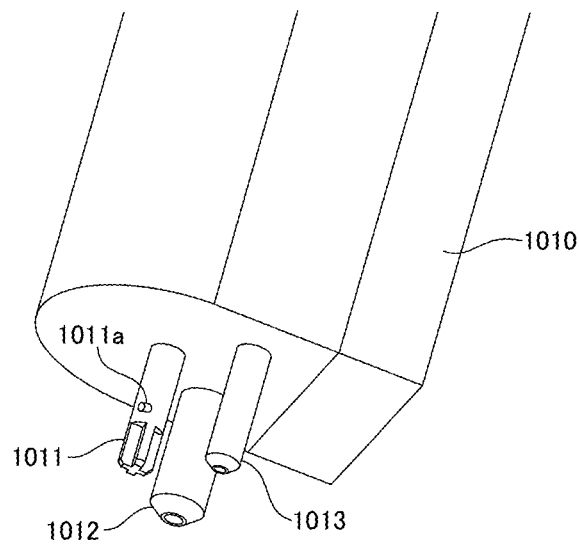
FIG. 15 is a simplified graphical representation of one embodiment of the tip part of the nozzle unit.

Next, the bead classification and recovery processing method performed by nucleic acid purification unit 140 of embodiments of the described invention will be described. Examples of the bead classification and recovery method comprise step (A1) to step (A12) as illustrated in FIGS. 6 to 9. In each step, the dispensing of the solution into each tube, the aspiration of the solution from each tube, the movement of the solution between the respective tubes, the addition and loading of reagents into each tube, the washing of the inside of each tube, and the like are performed using the dispensing burette 1012 (1013) of the nozzle unit (as illustrated in FIG. 15).

For example in step (A1) as illustrated in FIG. 6, the solution containing the broken emulsion with nucleic acid-bound beads is moved from emulsion breaking unit 130 to first tube 141, where the nucleic acid-bound beads are washed. In step (A2), melt-solution is added to first tube 141 to transform the double-stranded DNA on the nucleic acid-bound beads into single-stranded DNA with one strand remaining bound to the bead and a second strand in solution. In step (A3), an enriching primer is added first tube 141 and annealed to the single-stranded DNA immobilized on the bead by heating to 65° C. with the heat block 144.

Figure 7:
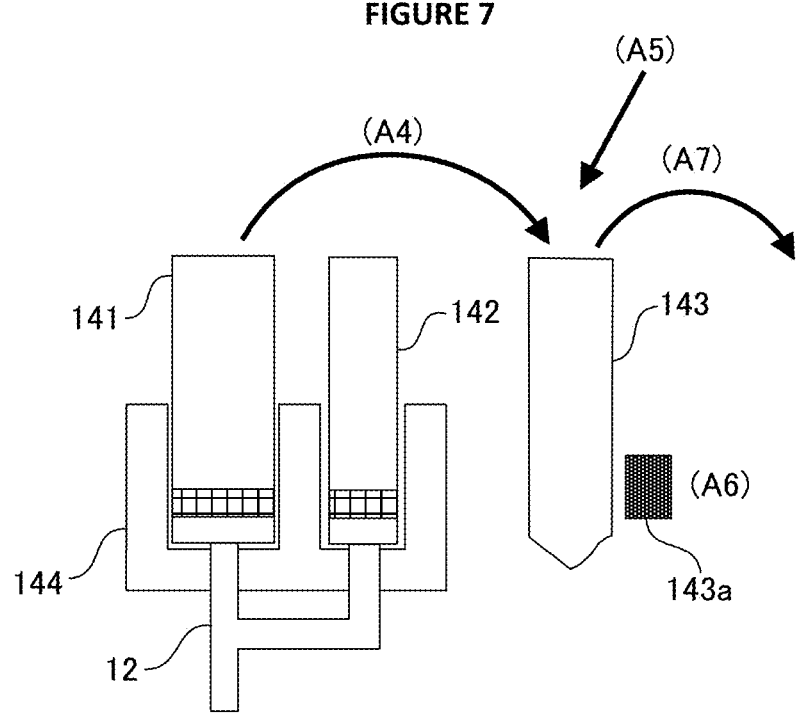
FIG. 7 is a simplified graphical representation of one embodiment of the processing following the processing of FIG. 6.

Continuing the example from above, in step (A4) as illustrated in FIG. 7, the nucleic acid-bound beads with annealed enrichment primers are moved from first tube 141 to third tube 143. In step (A5), magnetic beads are added to third tube 143, and the nucleic acid and magnetic beads bound to one another as described in the general principles above. In step (A6), magnet 143a is moved to an adsorption position that attracts and pulls the nucleic acid-bound beads against the side of third tube 143. In step (A7), beads that were not captured by the magnet 143a are discarded.

Figure 8:
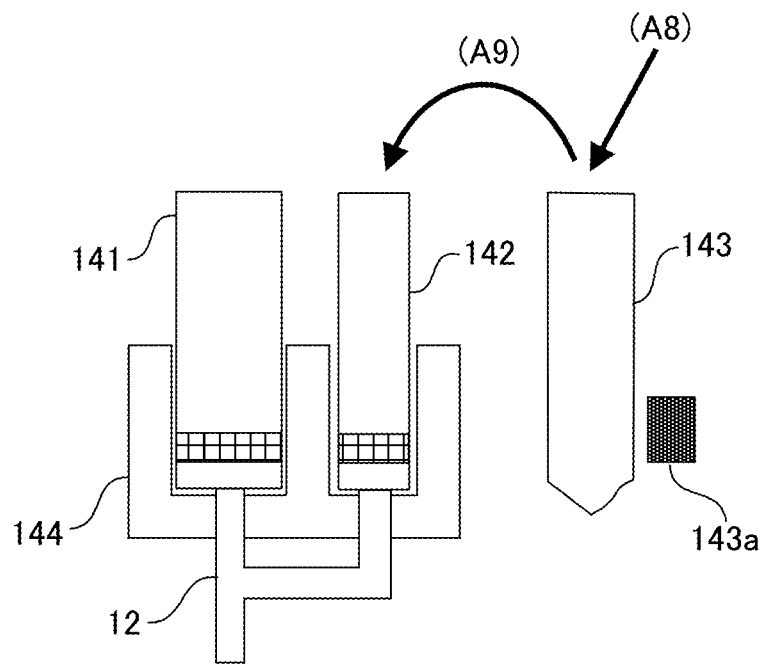
FIG. 8 is a simplified graphical representation of one embodiment of the processing following the processing of FIG. 7.
Figure 9:
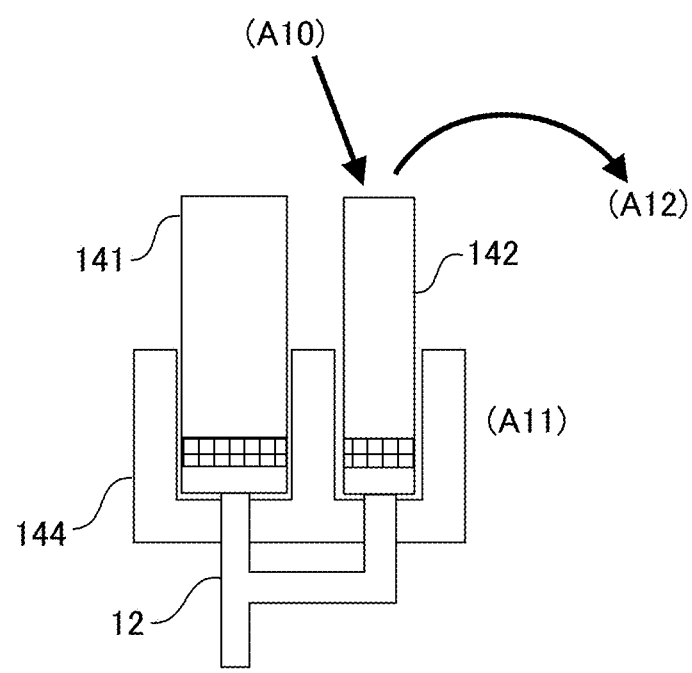
FIG. 9 is a simplified graphical representation of one embodiment of the processing following the processing of FIG. 8.

Further continuing with the described example, step (A8) as illustrated in in FIG. 8 melt-solution is added to third tube 143 to separate the magnetic beads and the nucleic acid-bound beads. In step (A9), the solution containing the nucleic acid-bound beads is moved from the third tube 143 to the second tube 142. Also, in step (A10) as illustrated in FIG. 9, a sequencing primer is added to second tube 142 and annealed to the bead bound DNA (by heating second tube 142 to 65° C. with heat block 144). In step (A11), the excess primer is removed by washing. In step (A12), the nucleic acid-bound beads are aspirated and transferred to a separate container to complete the bead classification and recovery process.

Figure 19:
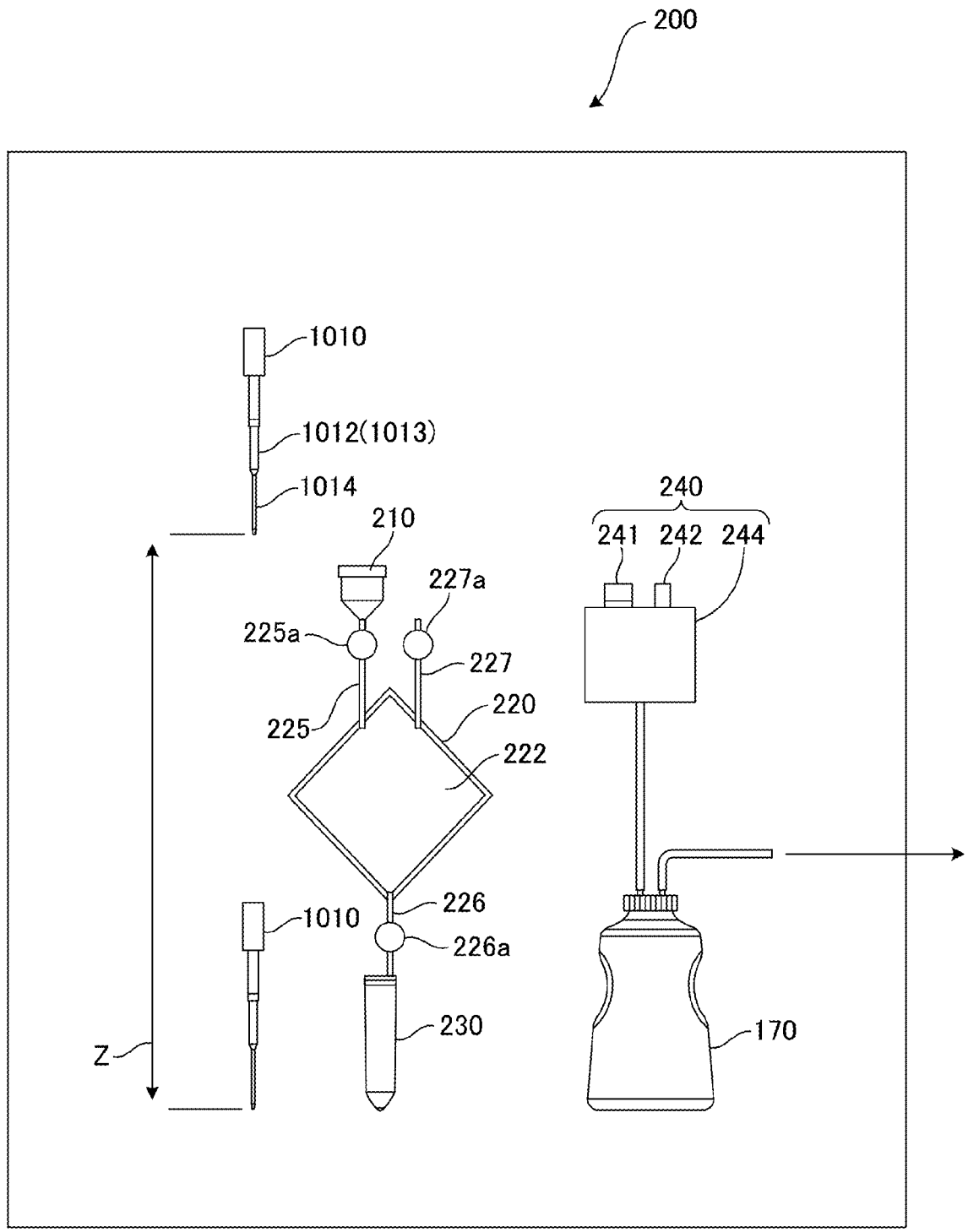
FIG. 19 is a simplified graphical representation of one embodiment of a first embodiment of a device.

In the described example, washing the beads inside first tube 141 is performed by aspirating only the solution from first tube 141 via first filter 141a with the suction force provided by vacuum trap 170 (as illustrated in FIG. 19). Similarly, the washing of the beads inside the second tube 142 is performed by aspirating only the solution from the solution containing the beads inside the second tube 142 via the second filter 142a with the suction force of the vacuum trap 170.

(4-3) Alternative Example of Bead Classification and Recovery Processing

An alternative example of the bead classification and recovery method comprises step (B1) to step (B11), as illustrated in FIGS. 10 to 13.

Figure 10:
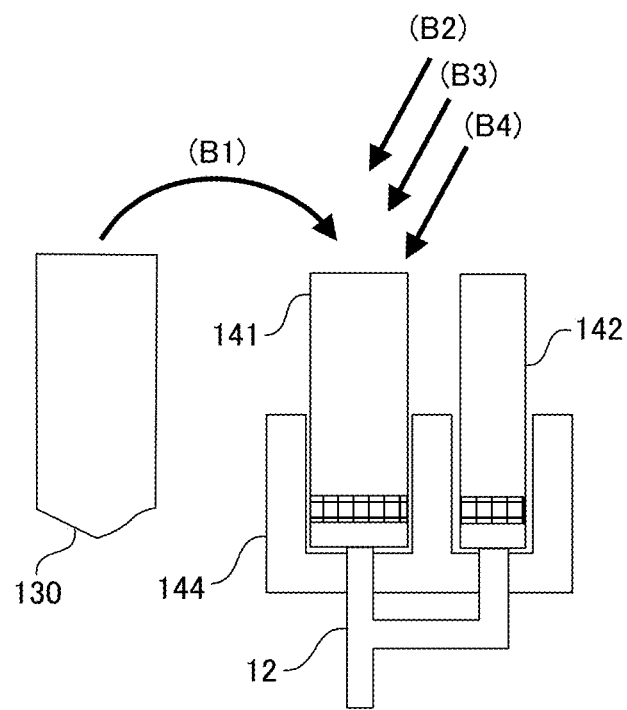
FIG. 10 is a simplified graphical representation of another embodiment of the processing of the nucleic acid purification unit.

Steps (B1) to (B3) in FIG. 10 are the same as steps (A1) to (A3) in FIG. 6, so an explanation of these steps will be omitted. In step (B4) as illustrated in FIG. 10, magnetic beads are added into first tube 141, where the magnetic beads and the nucleic acid-bound beads are bound to one another (magnetic bead-nucleic acid-bound bead conjugate).

Figure 11:
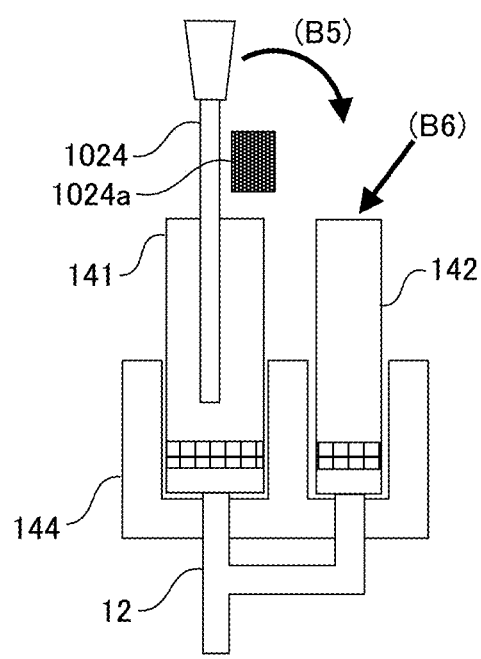
FIG. 11 is a simplified graphical representation of one embodiment of the processing following the processing of FIG. 10.

In step (B5) as illustrated in FIG. 11, the solution containing the magnetic bead-nucleic acid-bound bead conjugate is aspirated into a dispensing burette 1024, and only this conjugate is captured on the inside surface of the dispensing burette 1024 by a magnet 1024a and subsequently the captured conjugate is moved to second tube 142. Dispensing burette 1024 is provided with magnet 1024a and is connected to the nozzle unit 1010. In step (B6), melt-solution is added to second tube 142 to separate the magnetic beads and the nucleic acid-bound beads from the conjugate.

Figure 12:
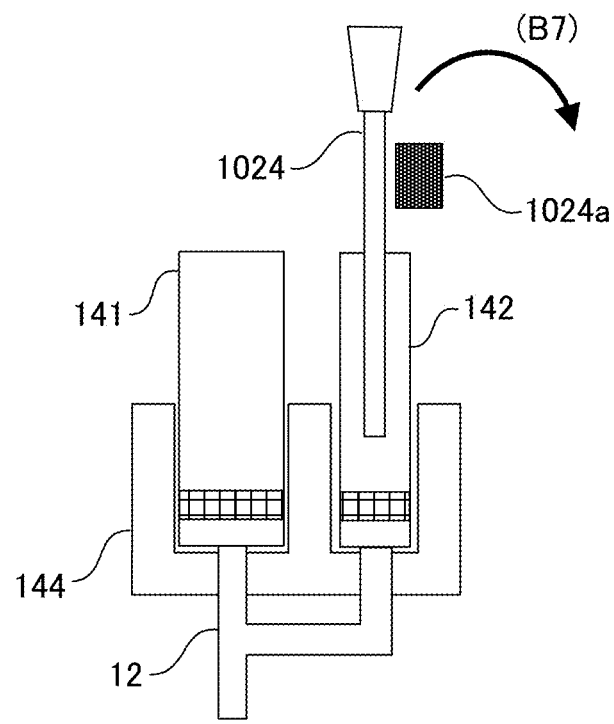
FIG. 12 is a simplified graphical representation of one embodiment of the processing following the processing of FIG. 11.
Figure 13:
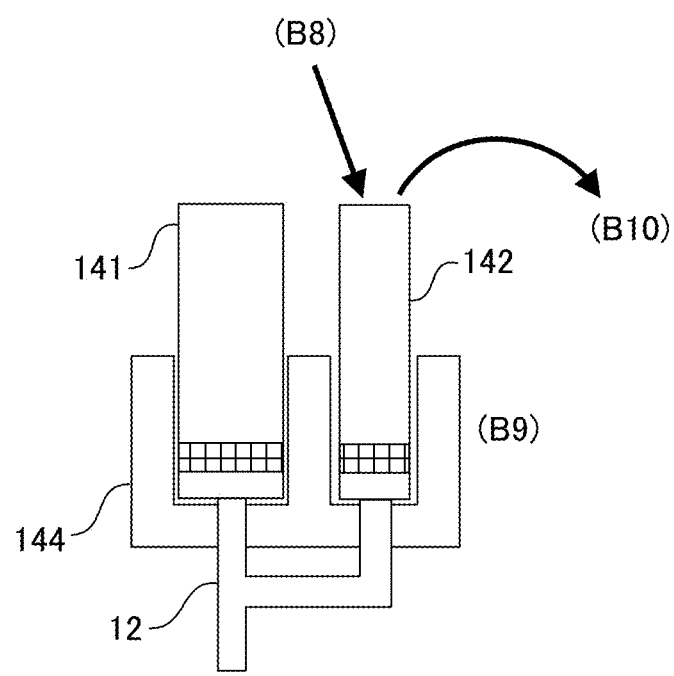
FIG. 13 is a simplified graphical representation of one embodiment of the processing following the processing of FIG. 12.

In step (B7) as illustrated in FIG. 12, the melt-solution inside second tube 142 is aspirated into the dispensing burette 1024 which dissociates the bond between the amplified nucleic acid molecules and enrichment primers. Thus only the magnetic beads separated by melt-solution are captured on the inside surface of burette 1024 by magnet 1024a. The melt solution with nucleic acid-bound beads is returned into the second tube 142. The captured magnetic beads may be discarded, but they may also be washed and reused in steps (B4) to (B6). In step (B8) in FIG. 13, a sequencing primer is added, and the sequencing primer is annealed to the DNA of the nucleic acid-bound beads (by heating the second tube 142 to 65° C. with heat block 144). In step (B9), the excess primer is removed by washing. In step (B10), the nucleic acid-bound beads are transferred to a separate container to complete the bead classification and recovery process.

3. Nucleic Acid Amplification Automation System

Figure 14:
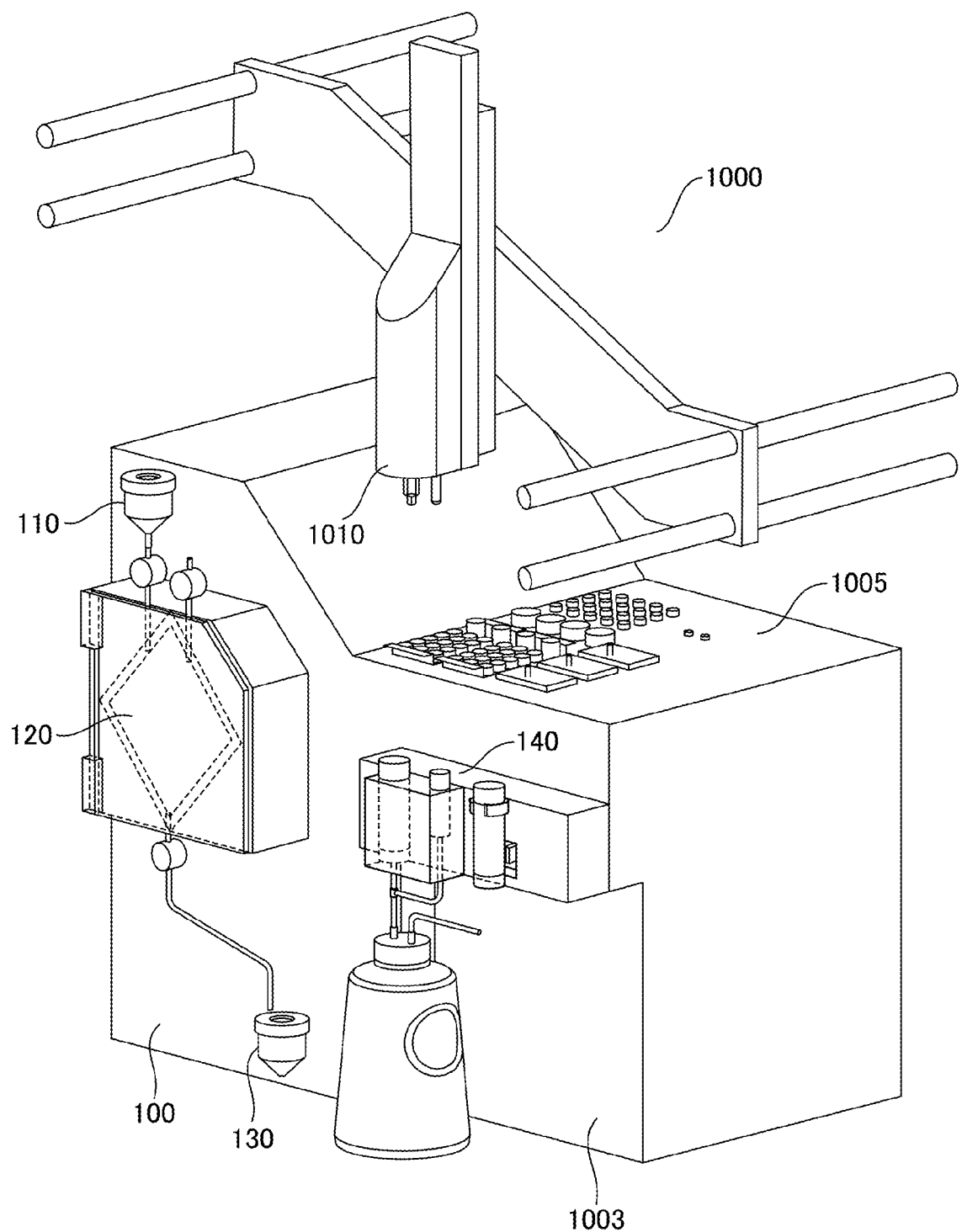
FIG. 14 is a simplified graphical representation of one embodiment of the nucleic acid amplification automation system.

An example of an embodiment of a nucleic acid amplification automation system (also simply called an "automation system") 1000 of the described invention is shown in FIG. 14 that includes automation device 100 mounted on the front surface 1003 of the system (side surface part of the device 100). In the described embodiment, automation system 1000 is provided with a nozzle unit (automatic processing mechanism) 1010 which can be moved three-dimensionally by a moving mechanism described below. Further, a microplate or the like having a plurality of tips for dispensing, dispensed reagents, samples, a cooling and heating block for reagents, and multiple wells is disposed on a stage 1005 on the upper surface of the system, and a mixing operation of the respective reagents can be performed on the stage 1005.

FIG. 15 is an illustrative example of an enlarged view of an embodiment of the tip part of the nozzle unit 1010 when viewed from below. Stirring rod connection part 1011 and first dispensing burette 1012 are disposed on the tip part of nozzle unit 1010, but a second dispensing burette 1013 may also be provided in accordance with the amount and type of the dispensed solution. For example, first dispensing burette 1012 can preferably dispense a relatively large volume of 500 μl to 5 ml of the solution, and second dispensing burette 1013 can dispense a relatively small volume of 5 μl to 500 μl of the solution.

In the described embodiments, stirring rod connection part 1011 is rotated or oscillated by stirring rod rotating motor 1105 (as illustrated in the functional block diagram of FIG. 17), and stirring rod 114 shown in FIG. 3 can also be connected to the tip of stirring rod connection part 1011 and rotated and/or oscillated. A stirring rod for stirring in order to remove unnecessary components such as oil from the solution containing the amplified nucleic acids within the emulsion breaking unit 130 may also be connected to this stirring rod connection part 1011. In this way, stirring rod connection part 1011, first dispensing burette 1012, and second dispensing burette 1013 can be formed with nozzle unit 1010 as an integrated unit. Further, stirring rod connection part 1011 can be established separately from the nozzle unit 1010. For example stirring rod connection part 1011 can be fixed to the upper parts of emulsion generation unit 110 and/or the emulsion breaking unit 130. In this case, first dispensing burette 1012 and second dispensing burette 1013 are disposed on the nozzle unit 1010, where the load on an X'-axis motor 1101, a Y-axis motor 1102, and a Z-axis motor 1103 (as illustrated in the functional block diagram of FIG. 17) described below can be reduced by reducing the size and weight of the nozzle unit 1010.

Figure 16:
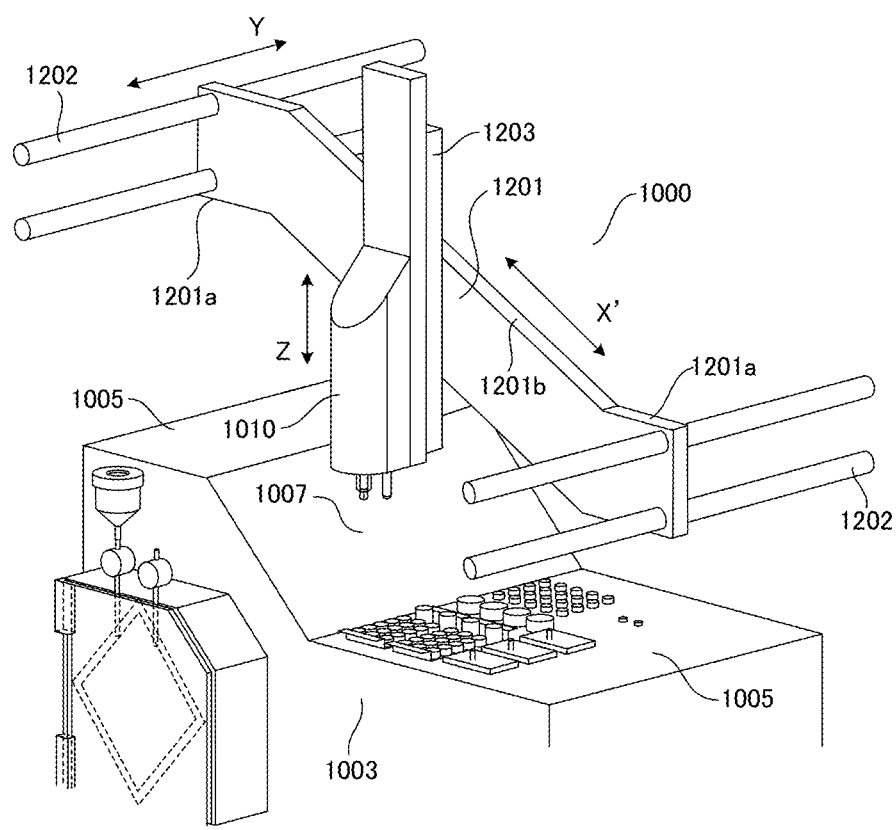
FIG. 16 is a simplified graphical representation of one embodiment of the movement direction of the nozzle unit.

FIG. 16 provides an illustrative example of one embodiment of a magnified view of the upper part of system 1000 showing the movement direction of nozzle unit 1010. Nozzle unit 1010 can respectively move in an inclined direction such as the X'-axis direction, the Y-axis direction, and the Z-axis direction. In the example of FIG. 16, nozzle unit 1010 travels along inclined direction guide member 1201, Y-axis direction guide member 1202, and Z-axis direction guide member 1203 in the space above stage 1005 and in the space to the side of system 1000 relative to front surface 1003. In the described embodiments, inclined direction guide member 1201 can move the nozzle unit 1010 in accordance with the slope of the inclined surface 1007 of the upper surface of the system. Inclined direction guide member 1201 is driven by X'-axis motor 1101 (as illustrated in the functional block diagram of FIG. 17), inclined direction guide member 1201 comprises a horizontal guide portion 1201a for moving the nozzle unit 1010 parallel to stage 1005 and inclined guide portion 1201b for moving the nozzle unit 1010 at an incline, so inclined direction guide member 1201 can move nozzle unit 1010 in accordance with the contour of the upper surface of the system.

In the embodiments described herein, liquid transfer from emulsion generation unit 110 to emulsion breaking unit 130 is performed using head drop as described above, so there is a difference in vertical positioning relative to the force of gravity between emulsion generation unit 110 and emulsion breaking unit 130. Accordingly, when accessing emulsion generation unit 110 and emulsion breaking unit 130, nozzle unit 1010 can shorten the stroke in the Z-direction by moving in the X'-axis direction inclined with respect to stage 1005 (horizontal surface).

FIG. 17 provides a functional block diagram of one embodiment of nucleic acid amplification automation system 1000 that comprises mechanical control part 1100 to which various instruments described below are attached and built-in personal computer (PC) 1200 operatively connected to mechanical control part 1100. For example, embodiments of mechanical control part 1100 typically comprise a temperature control part, a motor control part, an I/O control part, storage parts (RAM, ROM), a timekeeping part, and the like. Further, embodiments of built-in PC 1200 comprise a screen control part, a data management part, storage parts (RAM, ROM, HDD), a timekeeping part, and the like. In the same or alternative example embodiments may also comprise a display such as touch-panel display 1221 with a built-in operation interface and a display part operatively connected to built-in PC 1200

In the embodiments illustrated in FIG. 17, mechanical control part 1100 is operatively connected to X'-axis motor 1101 enabled to drive nozzle unit 1010 in the X'-axis (inclined axis) direction, Y-axis motor 1102 enabled to drive nozzle unit 1010 in the Y-axis direction, and Z-axis motor 1103 enabled to drive nozzle unit 1010 in the Z-axis direction. Mechanical control part 1100 is also operatively connected to, dispensing burette 1104 enabled to provide fluid pumping force for dispensing burettes 1012 and 1013 by driving a dispensing burette motor, stirring rod rotating motor 1105 enabled to rotate or oscillate stirring rod connection part 1011 to which the stirring rod is connected, and magnet moving motor 1106 enabled to move magnet 143a and/or 1024a for adsorbing magnetic beads.

Also, FIG. 17 includes position sensor 1108 enabled to detect the position of nozzle unit 1010, respective flow path opening and closing devices 125a (126a), and pressure sensor 1112 each operatively connected to the mechanical control part 1100. In the described embodiments, position sensor 1108 is respectively provided on X'-axis motor 1101, Y-axis motor 1102, and Z-axis motor 1103 so as to detect the positions on the respective axes and output the positions to mechanical control part 1100. Pressure sensor 1112 is respectively provided on first filter 141a of first tube 141 and second filter 142a of second tube 142 and detects the presence or absence of a liquid in each tube based on pressure changes (pressure changes caused by the solution passing through the filter). Further, vacuum pump 1114, emulsion generation unit water level sensor 1116 for measuring the water level (fluid volume) inside emulsion generation unit 110, and nucleic acid amplification unit water level sensor 1118 for measuring the water level (fluid volume) of nucleic acid amplification unit 120, all of which are operatively connected to mechanical control part 1100. Ultrasonic-type, floating-type, electrostatic capacitance-type, or pressure-type water level sensors, for example, can be used as water level sensors.

For example, emulsion generation unit water level sensor 1116 can confirm that the solution has been appropriately transferred by means of gravity flow from emulsion generation unit 110 to nucleic acid amplification unit 120 and detect that there is no residual quantity inside emulsion generation unit 110 after the transfer. Similarly, nucleic acid amplification unit water level sensor 1118 can confirm that the solution has been appropriately transferred by means of gravity flow from nucleic acid amplification unit 120 to emulsion breaking unit 130 and detect that there is no residual quantity inside the nucleic acid amplification unit 120 after the transfer.

In some embodiments, PCR temperature control part 1120 is connected to mechanical control part 1100, and temperature sensor 1120a for detecting the temperature of nucleic acid amplification unit 120 and Peltier unit 1121 for executing the heating and cooling of the nucleic acid amplification unit, all of which are operatively connected to the PCR control part 1120. Further, first heat block heating part 1122 disposed on heat block 144 of system front surface 1003, second heat block heating part 1124 disposed on stage 1005, and cool block cooling part 1126 disposed on stage 1005 are all operatively connected to mechanical control part 1100. Temperature sensors 1122a, 1124a, and 1126a are respectively operatively connected to first heat block heating part 1122, second heat block heating part 1124, and cool block cooling part 1126. Second heat block heating part 1124 heats a second heat block (not shown) on the stage and is used to denature DNA of the sample from double-stranded DNA to single-stranded DNA before performing PCR, to thaw frozen reagents prior to the initiation of preprocessing performed by the automatic processing system of the presently described invention, or to thaw reagents susceptible to sedimentation at the time of storage. Cool block cooling part 1126 cools a cool block (not shown) on stage 1005 and is used to freeze beads collected in the final stage of preprocessing or to freeze reagents.

Embodiments of nucleic acid amplification automation system 1000 can move nozzle unit 1010 to the space on stage 1005 or any position in the space next to system front surface 1003 roughly perpendicular to the stage 1005 by driving X'-axis motor 1101, Y-axis motor 1102, and Z-axis motor 1103 and can move nozzle unit 1010 into emulsion generation unit 110, emulsion breaking unit 130, nucleic acid purification unit 140, or onto stage 1005 to perform stirring processing, dispensing processing, or the like. In addition, nucleic acid amplification automation system 1000 can execute the PCR cycle by controlling the environment within reaction vessel 122 to a prescribed temperature with PCR temperature control part 1119 by heating or cooling using Peltier unit 1121 based on the temperature detected by temperature sensor 1120 in nucleic acid amplification unit 120. Further, nucleic acid amplification automation system 1000 can purify the nucleic acids in solution by controlling the pumping of dispensing burettes 1012 and 1013 using dispensing burette motor 1104 in nucleic acid purification unit 140.

Figure 18:
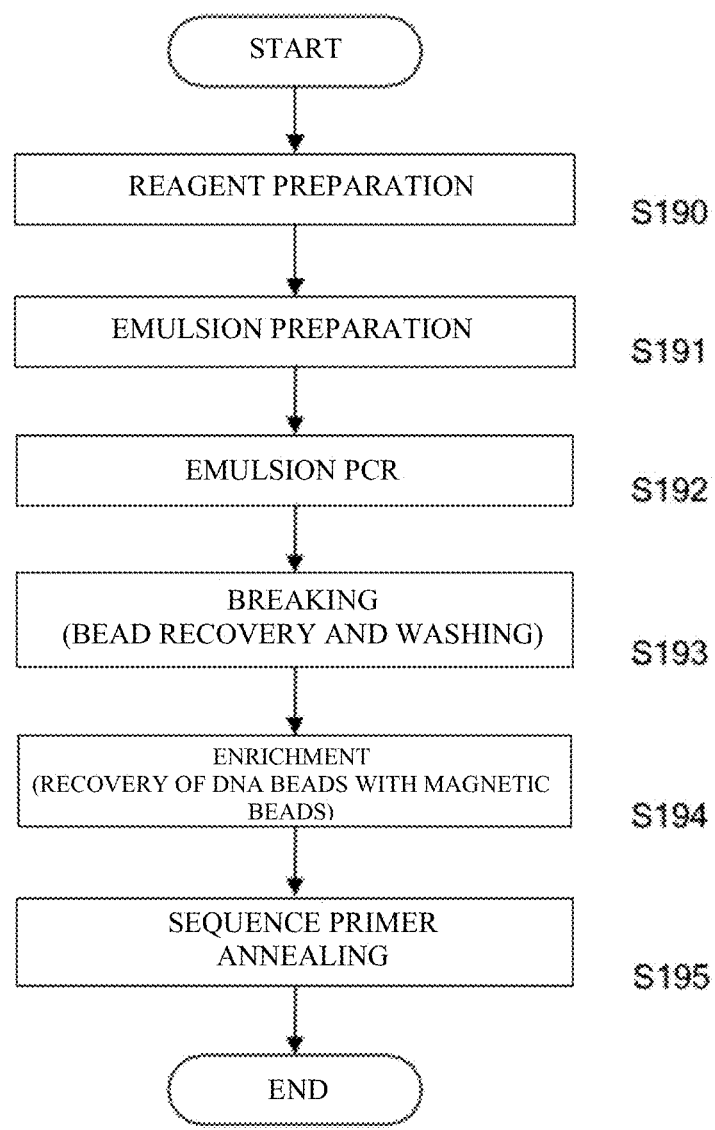
FIG. 18 is a simplified graphical representation of one embodiment of a flowchart showing the processing procedure executed by the nucleic acid amplification automation system.

An overview of the processing executed using nucleic acid amplification automation system 1000 is illustrated in the steps of the flowchart provided in FIG. 18. First, reagents are prepared in step S190. In step S191, an emulsion is generated by emulsion preparation using dispensing burette 1012 (1013) of nozzle unit 1010 within emulsion generation unit 110. Next, in step S192, the solution containing the prepared reagents and emulsion is transferred by means of gravity flow to nucleic acid amplification unit 120, and emulsion PCR is executed. In step S193, after the solution is transferred by means of gravity flow from nucleic acid amplification unit 120 to emulsion breaking unit 130 and breaking is performed, the nucleic acid-bound beads are recovered and washed. In step S194, the beads recovered in step S193 are transferred to nucleic acid purification unit 140, where enrichment (recovery of nucleic acid-bound beads by magnetic beads) is performed. In step S195, after a sequencing primer is annealed to the recovered nucleic acid-bound beads, the excess primer is removed, and the remaining recovered nucleic acid-bound beads are recovered to end the process.

Embodiments of the system invention will be described more specifically hereinafter as specific configurations. Explanations of processing that is the same for each configuration of unit or instruments similarly used for each configuration will be omitted. However, the present invention is not limited to these embodiments.

(Embodiment 1)

Device 200 of Embodiment 1 is described herein with reference to the schematic diagram of FIG. 19. In the described embodiment, device 200 comprises nozzle unit 1010, emulsion generation unit 210, nucleic acid amplification unit 220, emulsion breaking unit 230, nucleic acid purification unit 240, and vacuum trap 170 connected to a vacuum pump not shown in the drawing.

Further, nozzle unit 1010 is provided with dispensing burettes 1012 and 1013 (also illustrated in FIG. 15). Nozzle unit 1010 can also be moved in three dimensions by motors 1101 to 1103 (as illustrated in FIG. 17). The pumping of dispensing burettes 1012 and 1013 and the driving of nozzle unit 1010 are controlled by mechanical control part 1100. In addition, disposable tips 1014 are attached to the tips of dispensing burettes 1012 and 1013. Accordingly, dispensing burette 1012 of nozzle unit 1010 enables the injection of the solution into each unit or the aspiration of the solution from each unit, and the driving part enables the transfer of the solution between the respective units. For example, as shown in FIG. 16, since nozzle unit 1010 can move in the Z-axis direction (vertical direction), the solution can be injected into emulsion generation unit 210 or the solution can be aspirated from and injected into emulsion breaking unit 230.

Also in the described embodiments, nucleic acid amplification unit 220 preferably comprises reaction vessel 222 comprising a volume of 40 ml and a Peltier device (not shown) capable of heating and cooling reaction vessel 222. Reaction vessel 222 comprises a first liquid transfer channel 225 for connecting the lower part of emulsion generation unit 210 and the upper part of reaction vessel 222, a second liquid transfer channel 226 connected to the lower part of reaction vessel 222, and a third liquid transfer channel 227 connected to the upper part of reaction vessel 222. Liquid transfer channels 225, 226, and 227 are operatively connected to pinchcock-like channel opening and closing devices 225a, 226a, and 227a, respectively. Emulsion breaking unit 230 typically comprises a container with a volume of 100 ml and is disposed on the lower end of second liquid transfer channel 226.

Additionally, nucleic acid purification unit 240 comprises a first tube 241 equipped with a first filter not shown in the drawing, a second tube 242 equipped with a second filter not shown in the drawing, and heat block 244 for heating both tubes. Vacuum trap 170 is connected to the respective tubes 241 and 242, and filtering and the like can be performed using the suction force of the vacuum trap 170.

Next, an overview of processing of the device 200 of Embodiment 1 will be given. First, each solution and the like is injected into emulsion generation unit 210 using dispensing burette 1012 of nozzle unit 1010, and this is stirred to generate an emulsion solution. Various solutions can be prepared from the reagents disposed on stage 1005 on the upper surface of the system.

The emulsion solution generated by emulsion generation unit 210 is allowed to drop down via first liquid transfer channel 225 and is housed in nucleic acid amplification unit 220. Nucleic acid amplification unit 220 amplifies the nucleic acids by executing a prescribed thermal cycle. When the amplification of the nucleic acids is complete, the solution containing the amplified nucleic acids is allowed to drop down via second liquid transfer channel 226 and is housed in emulsion breaking unit 230. Emulsion breaking unit 230 breaks the emulsion. Dispensing burette 1012 of the nozzle unit 1010 pumps out the broken solution and moves the solution into nucleic acid purification unit 240 that separates and purifies the nucleic acids contained in the solution using the respective tubes 241 and 242, heat block 244, and vacuum trap 170.

(Embodiment 2)

Figure 20:
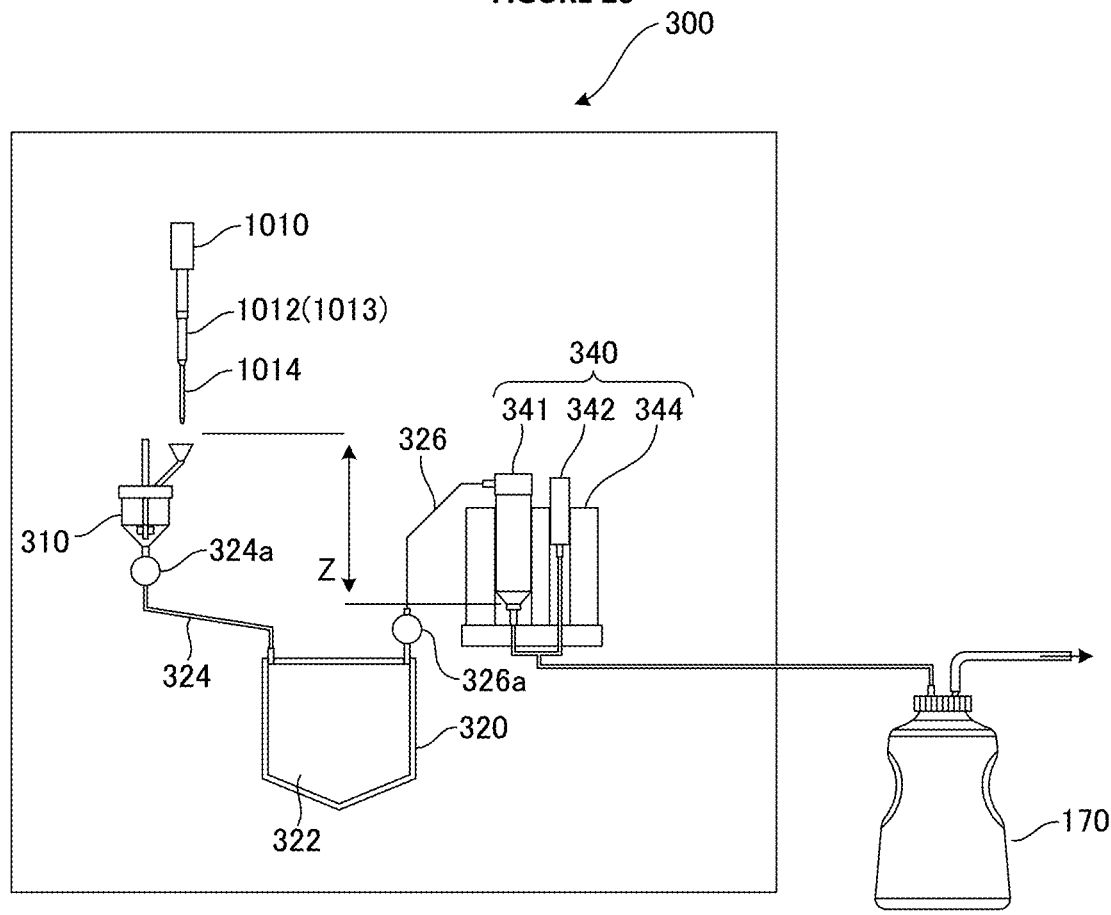
FIG. 20 is a simplified graphical representation of one embodiment of a second embodiment of a device.

Device 300 of Embodiment 2 is described herein with reference to the schematic diagram of FIG. 20. In the described embodiment, device 300 comprises nozzle unit 1010, emulsion generation unit 310, nucleic acid amplification unit 320, breaking and nucleic acid purification unit 340, and vacuum trap 170 connected to a vacuum pump not shown in the drawing, where vacuum trap 170 is connected to the breaking and nucleic acid purification unit 340.

In Embodiment 2, device 300 comprises a first liquid transfer channel 324 for connecting emulsion generation unit 310 and PCR unit 320, and a second liquid transfer channel 326 for connecting nucleic acid amplification unit 320 and breaking and nucleic acid purification unit 340. First liquid transfer channel 324 is disposed below emulsion generation unit 310 and is provided with a pinchcock-like channel opening and closing device 324a. Accordingly, when channel opening and closing device 324a is opened, the solution inside the emulsion generation unit 310 drops down through the first liquid transfer channel 324 due to gravity and is transferred to nucleic acid amplification unit 322.

Figure 21:
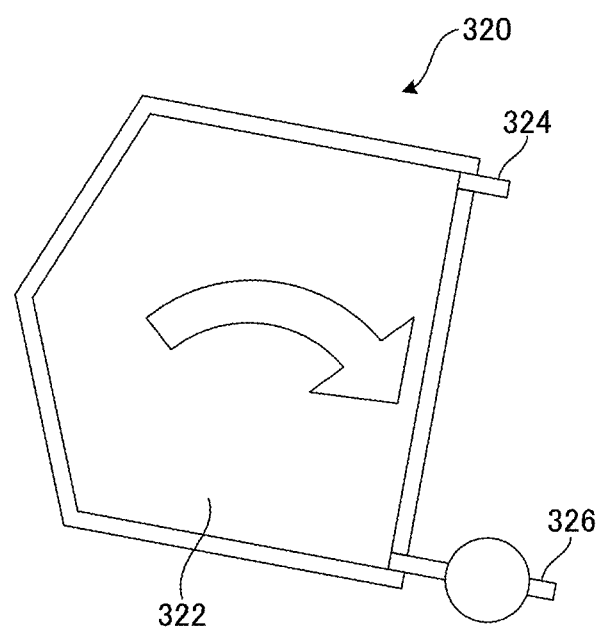
FIG. 21 is a simplified graphical representation of one embodiment of a front view showing the state of rotation of the nucleic acid amplification unit of FIG. 20.

Further, nucleic acid amplification unit 320 can be formed as a polygonal reaction vessel and, as shown in FIG. 21, may be provided with a pentagonal reaction vessel 322. For example, first liquid transfer channel 324 is connected to one end on the upper part of reaction vessel 322 and second liquid transfer channel 326 connected to the other end on upper part of the reaction vessel 322. Further, as shown in FIG. 21, nucleic acid amplification unit 320 may also be configured so that it can rotate at least 90 degrees, and is typically equipped with a rotating mechanism capable of rotating around the normal line axis at an arbitrary position on the plane thereof. Further, in order to allow nucleic acid amplification unit 320 to rotate, first liquid transfer channel 324 and second liquid transfer channel 326 may be configured so as to be flexible or detachable. As a result, nucleic acid amplification unit 320 can rotate at least 90 degrees, and the efflux of the solution inside reaction vessel 322 is accelerated in this state.

Figure 22:
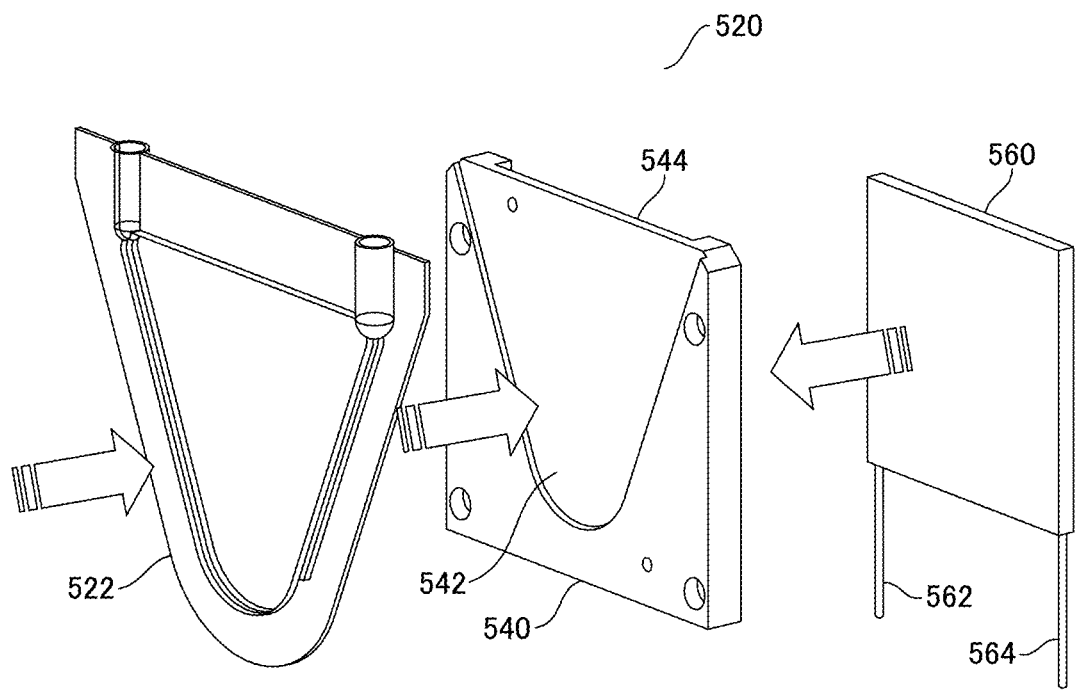
FIG. 22 is a simplified graphical representation of one embodiment of an exploded view showing the nucleic acid amplification unit of FIG. 20.
Figure 23:
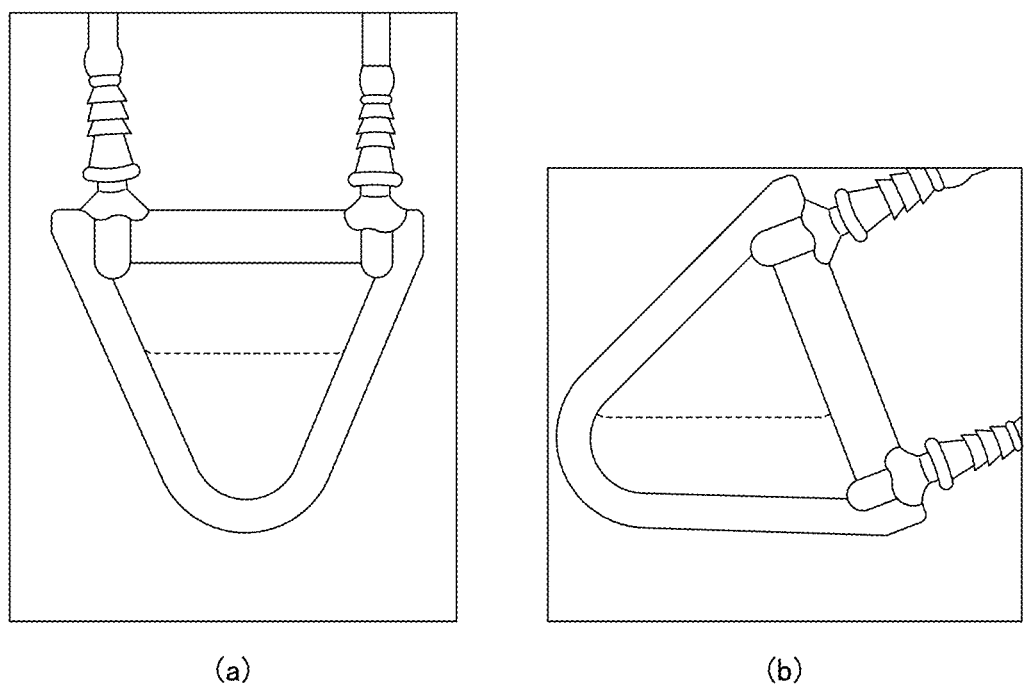
FIGS. 23A and B are simplified graphical representations of one embodiment of the state of usage of the PCR card of FIG. 22.

An embodiment of nucleic acid amplification unit 520 used in Embodiment 2 is described herein using FIGS. 22 and 23. It will also be appreciated that nucleic acid amplification unit 520 can be used as the nucleic acid amplification unit of other embodiments or modes. As shown in the exploded oblique view of FIG. 22, nucleic acid amplification unit 520 comprises PCR card 522 serving as a flat, bag-like reaction vessel, PCR plate 540 for holding the PCR card 522 (with a roughly triangular shape in this case), and thermal module 560 for heating PCR card 522 via the PCR plate 540. A Peltier device is preferably used as thermal module 560, but the module is not limited to a Peltier device, and another heating means may also be used.

In the described embodiment, the concave part 542 for housing PCR card 522 is formed on one side of PCR plate 540, and the concave part 544 for housing thermal module 560 is formed on the other side of PCR plate 540. PCR plate 540 is typically formed from a metal material with high thermal conductivity such as aluminum. Thermal module 560 has a pair of electrodes 562 and 564 and can be controlled to receive power and to be heated and cooled by a control part not shown in the drawing. The exposed surface side not housed in PCR plate 540 of PCR card 522 is covered with an insulating material not shown in the drawing.

FIG. 23 provides an illustrative example of PCR card 522 positioned (a) in the horizontal state and (b) in the inclined state. In FIG. 23 (a) the solution is held horizontally inside PCR card 522 away from both the influx port and the efflux portion. On the other hand, in FIG. 23 (b) PCR card 522 is inclined so that the solution inside reaction vessel 522 can flow out from the efflux port. In the described embodiment, PCR card 522 can be automatically rotated between the horizontal state and the inclined state by a rotating means (not shown).

As illustrated in FIG. 20, breaking and nucleic acid purification unit 340 comprises a first tube 341, a second tube 342, and heat block 344. First tube 341 has a first filter and typically has a volume of 50 ml. Second tube 342 has a second filter and typically has a volume of 5 ml. First tube 341 and second tube 342 can be heated to a prescribed temperature by heat block 344. Further, vacuum trap 170 is connected to both tubes 341 and 342 so that the tubes are decompressed. When first tube 341 or second tube 342 is decompressed, the solution inside first tube 341 or second tube 326 can be filtered by the first filter or the second filter provided inside first tube 341 or second tube 342.

Figure 24:
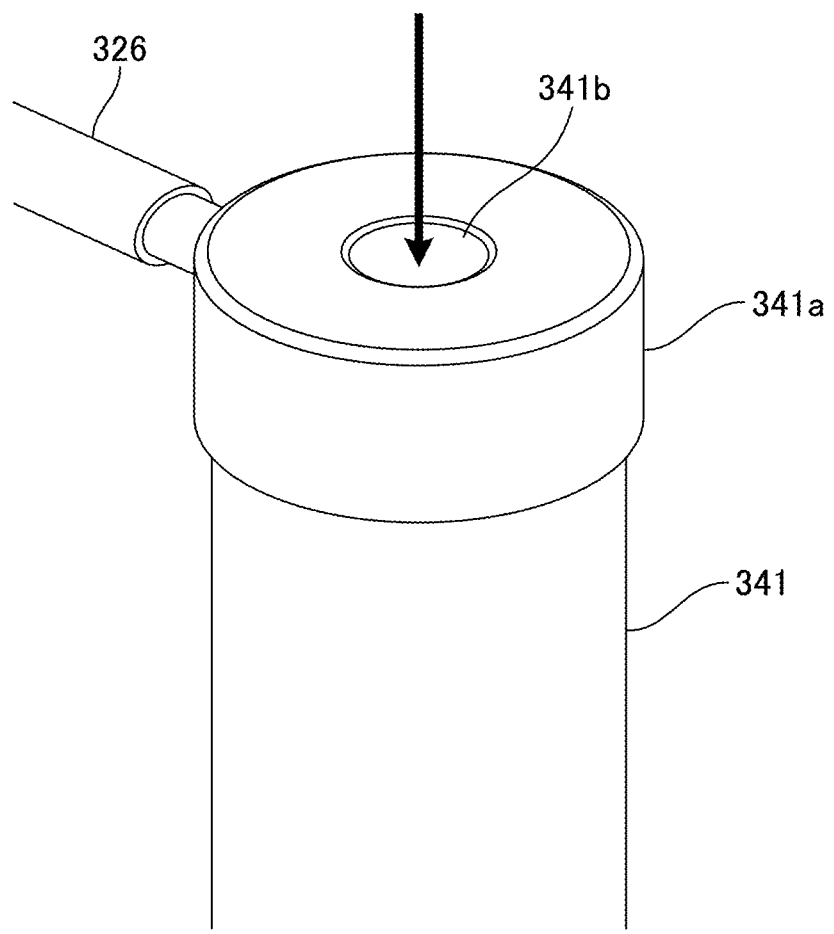
FIG. 24 is a simplified graphical representation of one embodiment of the cap of the first liquid transfer channel of FIG. 20.

FIG. 24 provides an illustrative example of an enlarged view of first tube 341 that comprises cap 341a detachably coupled to the upper part of the first tube 341, and penetrable part 341b formed on the upper surface of the cap 341a which can be penetrated by a dispensing burette or a dispensing tip. In the described embodiment, penetrable part 341b can be pierced by a nozzle, a syringe, or the like. Further, second liquid transfer channel 326 is connected to cap 341a.

Next, an overview of the processing of the device 300 of Embodiment 2 is described. First, each solution and the like is loaded into emulsion generation unit 310 using dispensing burette 1012, and the solution is stirred to generate an emulsion. Channel opening and closing device 324a of first liquid transfer channel 324 is opened so as to transfer the emulsion by means of gravity flow from emulsion generation unit 310 to nucleic acid amplification unit 320 via first liquid transfer channel 324. Nucleic acid amplification unit 320 amplifies the nucleic acids by executing a prescribed thermal cycle. The emulsion containing the amplified nucleic acids is then transferred from nucleic acid amplification unit 320 to breaking and nucleic acid purification unit 340 by the suction force of vacuum trap 170 via second liquid transfer channel 326 by opening channel opening and closing device 326a. Breaking and nucleic acid purification unit 340 breaks the emulsion, separates and purifies the beads comprising immobilized nucleic acids using respective tubes 341 and 342, heat block 344, and vacuum trap 170.

(Embodiment 3)

Figure 25:
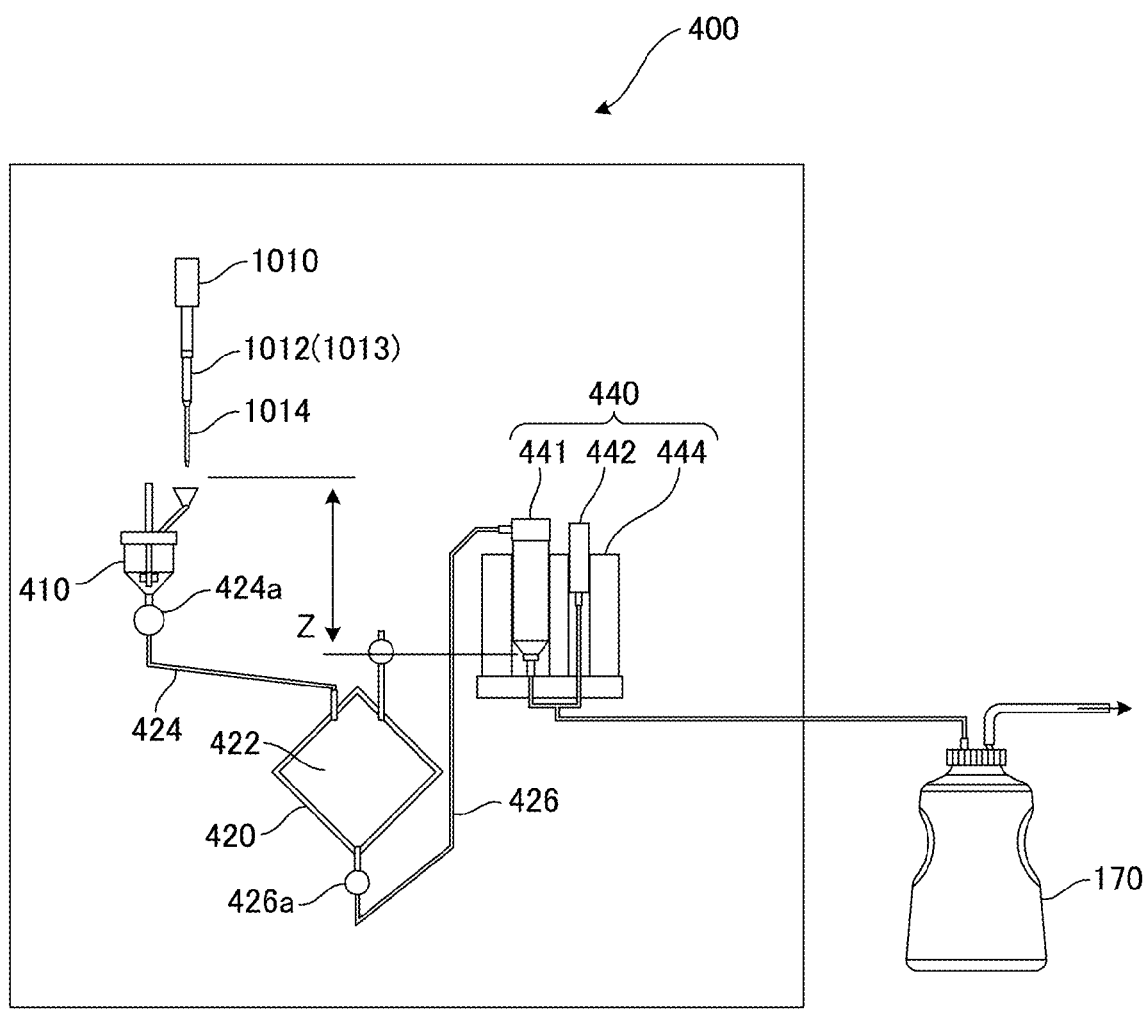
FIG. 25 is a simplified graphical representation of one embodiment of a third embodiment of a device.
Figure 26:
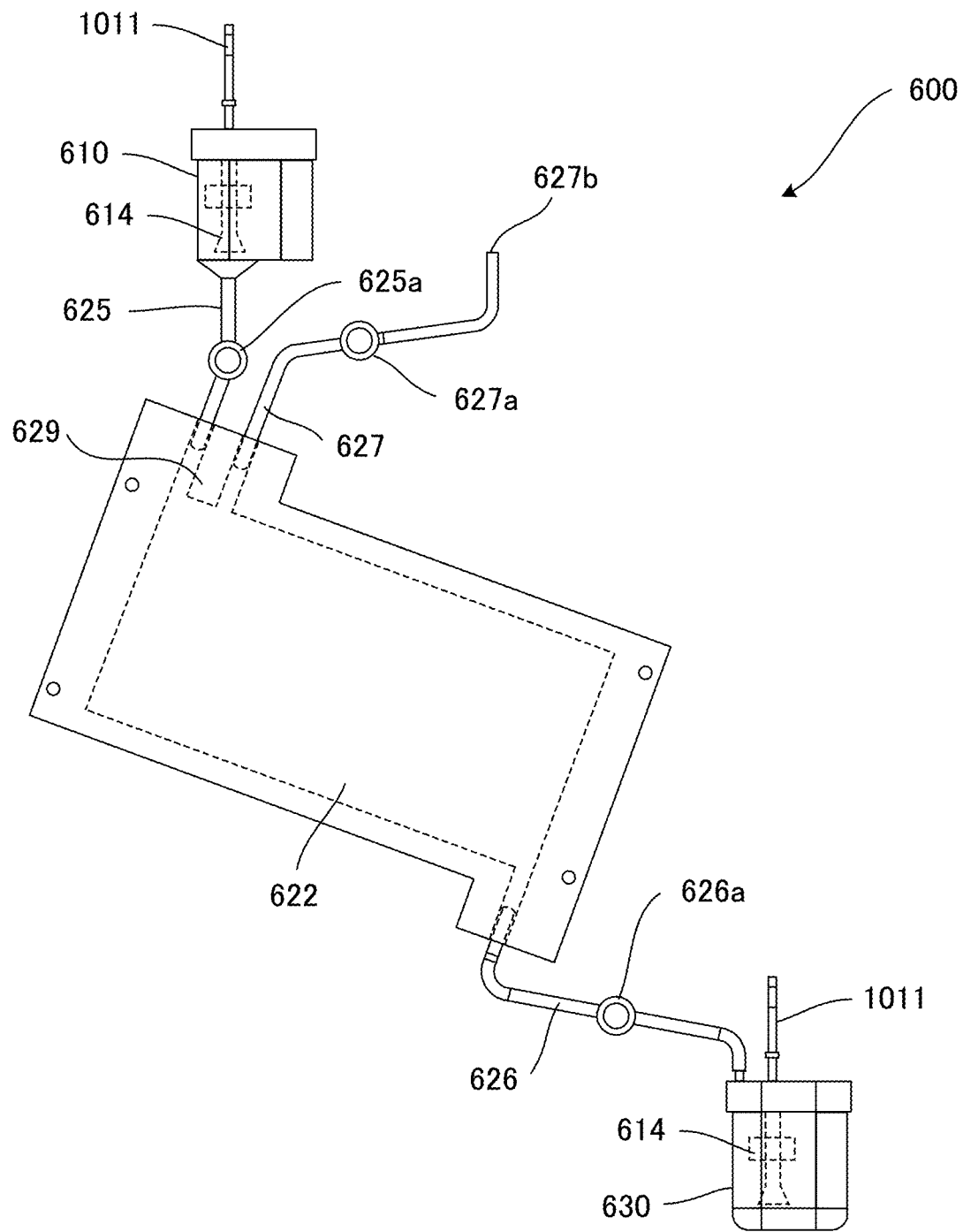
FIG. 26 is a simplified graphical representation of one embodiment of a fourth embodiment of a device.

A device 400 of Embodiment 3 is described herein with reference to the schematic diagram of FIG. 25. In the described embodiment, device 400 comprises nozzle unit 1010, emulsion generation unit 410, nucleic acid amplification unit 420 provided with reaction vessel 422, and breaking and nucleic acid purification unit 440. An embodiment of vacuum trap 170 connected to a vacuum pump not shown in the drawing is further connected to breaking and nucleic acid purification unit 440. First liquid transfer channel 424 connects emulsion generation unit 410 and nucleic acid amplification unit 420, and second liquid transfer channel 426 connects nucleic acid amplification unit 420 and breaking and nucleic acid purification unit 440. Pinchcock-like channel opening and closing devices 424a and 426a are respectively disposed on first liquid transfer channel 424 and second liquid transfer channel 426. In Embodiment 3, one end of second liquid transfer channel 426 is connected to the lower end of reaction vessel 422 of nucleic acid amplification unit 420. The other end of second liquid transfer channel 426 is connected to breaking and nucleic acid purification unit 440.

Next, an overview of processing of the device 400 of Embodiment 3 is described. First, each solution and the like is loaded into the emulsion generation unit 410 using dispensing burette 1012, and the solution stirred to generate an emulsion. Circuit opening and closing device 424a of first liquid transfer channel 424 is opened so as to transfer the emulsion by means of gravity flow from emulsion generation unit 410 to nucleic acid amplification unit 420 via first liquid transfer channel 424. Nucleic acid amplification unit 420 amplifies the nucleic acids by executing a prescribed thermal cycle. The emulsion containing the amplified nucleic acids is then transferred from nucleic acid amplification unit 420 to breaking and nucleic acid purification unit 440 by the suction force of vacuum trap 170 via second liquid transfer channel 426 in a state in which channel opening and closing device 426a is opened. Breaking and nucleic acid purification unit 440 breaks the emulsion, separates and purifies the beads comprising immobilized nucleic acids contained in the solution using respective tubes 441 and 442, heat block 444, and vacuum trap 170.

(Embodiment 4)

Figure 27:
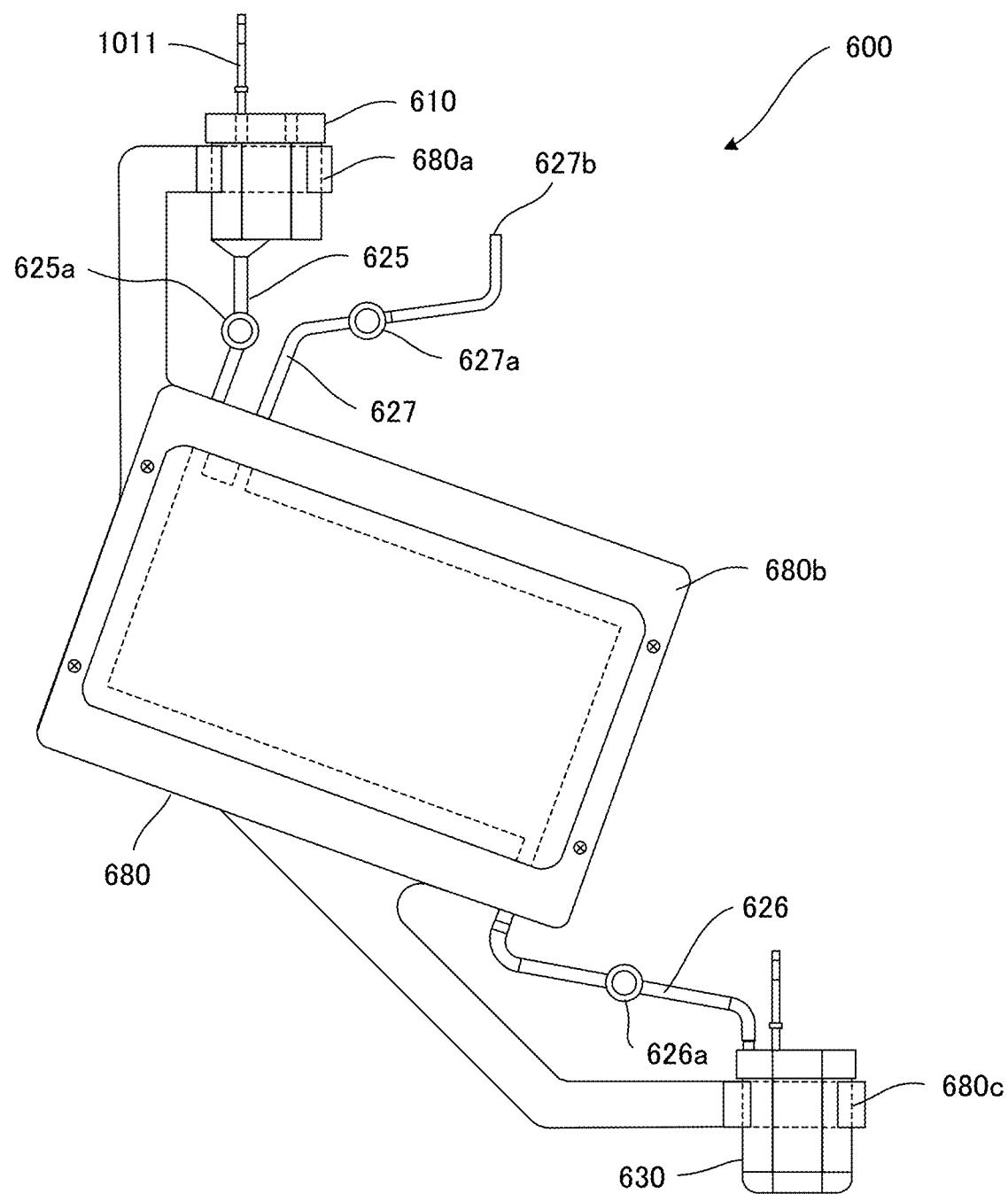
FIG. 27 is a simplified graphical representation of one embodiment of the state in which the frame is mounted on the device of FIG. 26.
Figure 28:
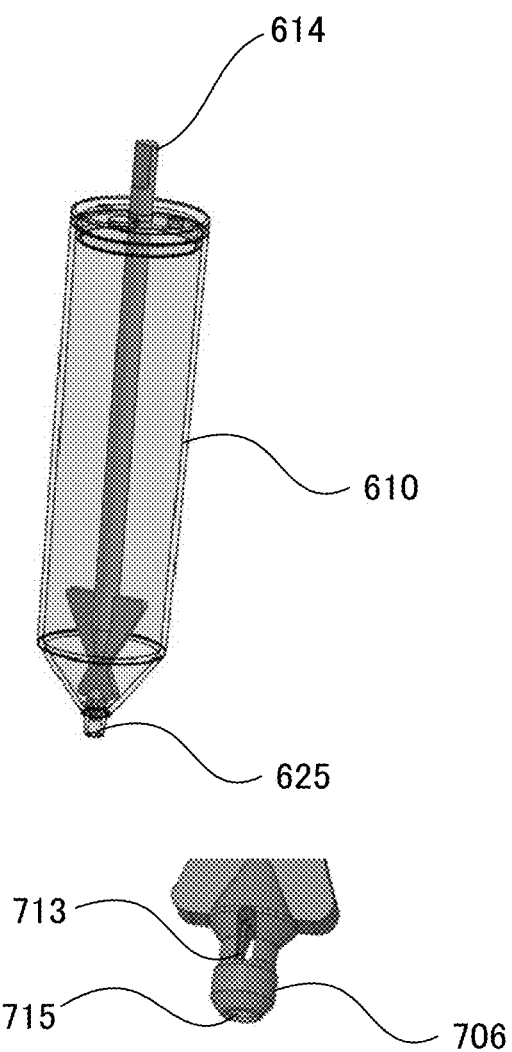
FIG. 28 is a simplified graphical representation of one embodiment of a stirring rod comprising a drain element.

Device 600 of Embodiment 4 is described herein with reference to the schematic diagrams of FIGS. 26 through 29. In the described embodiment device 600 comprises emulsion generation unit 610, reaction vessel 622, and emulsion breaking unit 630. A first liquid transfer channel 625 connects the lower part of emulsion generation unit 610 and the upper part of reaction vessel 622 via a tube for filling, and a second liquid transfer channel 626 connects the lower part of reaction vessel 622 and the upper part of emulsion breaking unit 630 via a tube for draining reaction vessel 622. A third air vent channel 627 is connected to the upper part of reaction vessel 622 via a tube that provides an air break which enables reliable filling and draining and in some embodiments enables filling without the need for sensors or changing the angle of reaction vessel 622 relative to gravity (i.e. tipping). Pinchcock-like channel opening and closing devices 625a, 626a, and 627a are respectively disposed on first liquid transfer channel 625, second liquid transfer channel 626, and third air vent channel 627. Stirring rod 614 comprising blades is operatively coupled to stirring rod connection part 1011 of a nozzle unit 1010 (not shown) can be moved into emulsion generation unit 610 or emulsion breaking unit 630 so as to stir the contents of each unit. In some embodiments, stirring rod 614 may also be constructed with an incorporated drain element. For example, FIG. 28 provides an illustrative example of one possible embodiment of stirring rod 614 that includes axle protrusion 706 constructed to fit into first liquid transfer channel 625 at the base of emulsion generation unit 610. Importantly, the fit between axle protrusion 706 and first liquid transfer channel 625 allows stirring rod 614 to freely spin while minimizing the amount of vibration caused by spinning FIG. 28 also illustrates slot 713 that allows fluid entry into interior channel 715 when inserted into emulsion generation unit 610 where the fluid can then be transferred through to first liquid transfer channel 625 via interior channel 715 by means of gravity flow as described elsewhere herein.

Device 600, as described herein, includes an embodiment of nucleic acid amplification unit 120 (as provided in the general device illustration of FIG. 5) comprises a substantially planar temperature control module that includes one or more thermoelectric devices such as Peltier devices (not shown) to perform thermal cycling operations required by PCR. For example, in some embodiments a configuration of 6-dual Peltier devices are individually programmable and spatially arranged to provide improved thermal control and increased flexibility with respect to power consumption.

Figure 29A:
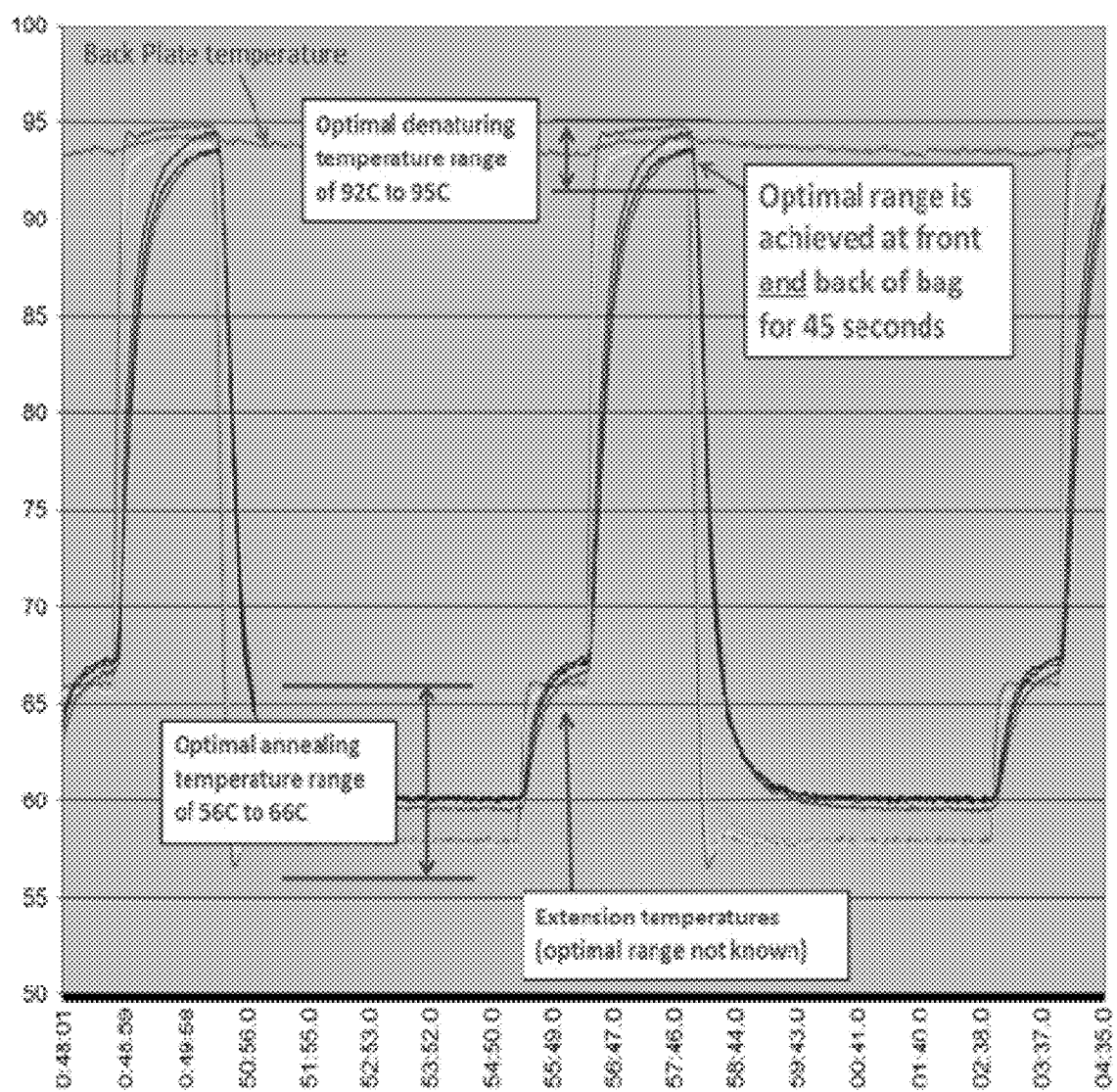
FIGS. 29A and 29B are simplified graphical representations of a comparison of data obtained from one embodiment of a nucleic acid amplification unit with a heated back plate.
Figure 29B:
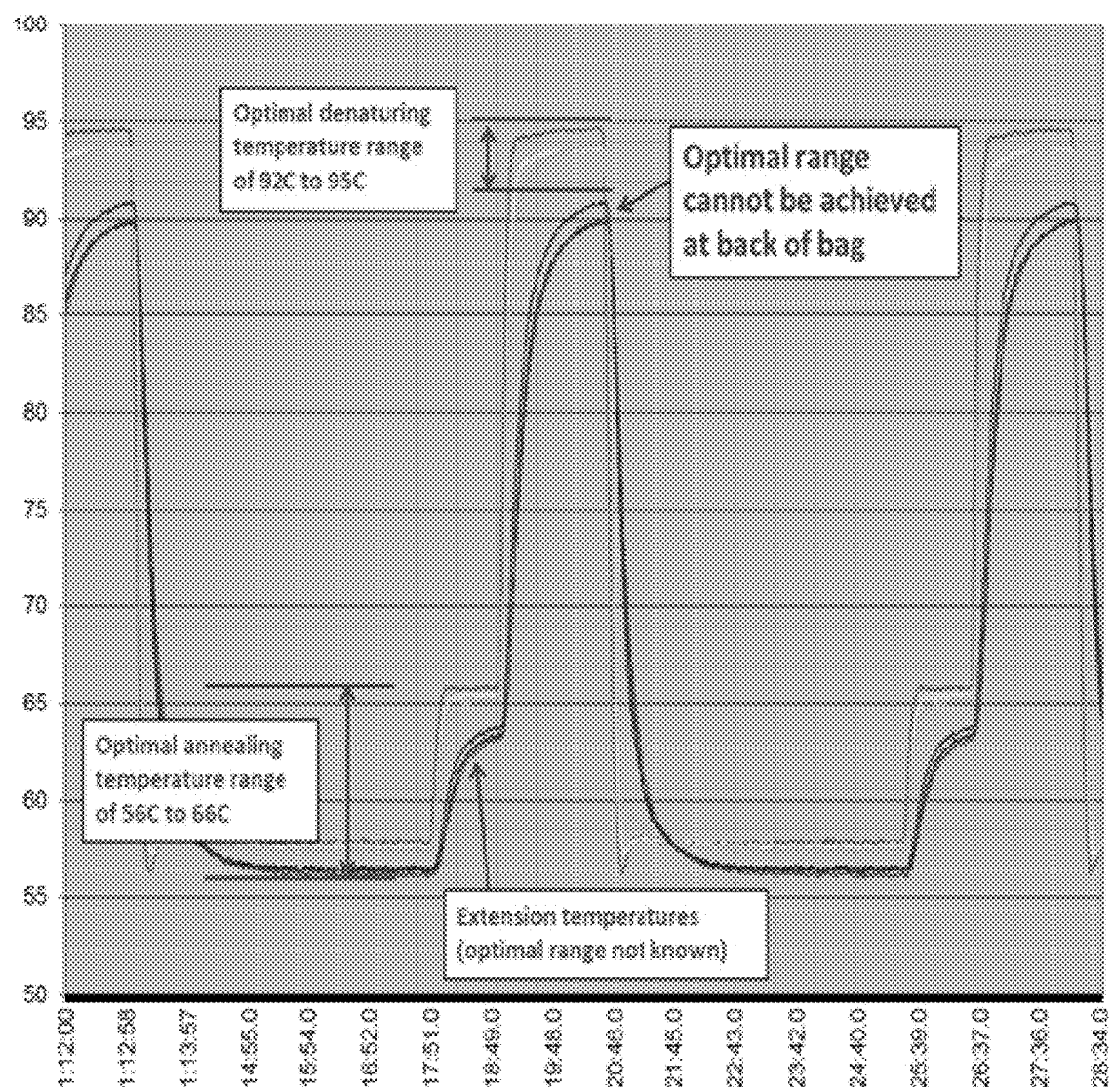

Further, device 600 comprises a substantially planar heated back plate in addition to an insulating layer positioned in an opposed relationship from the temperature control module with reaction vessel 622 sandwiched there between, similar to the example of cover 124 illustrated in FIG. 5. In the described embodiments, the heated back plate comprises a simple low cost heating element combined with at least one insulation layer positioned between the heating element and reaction vessel. In one embodiment of operation, the heated back plate provides a substantially constant temperature of at least 94° C. Alternatively, the heated back plate provides a substantially constant temperature of 100° C. or greater to increase the ramp rate at the insulation side of the reaction vessel. In this case, during denaturing, the temperature control module would hold its side of the vessel at 92° C. Further, in some embodiments that heated back plate may slowly thermally cycle, but the primary thermal cycling responsibility would still be performed by the temperature control module. FIGS. 29A and 29B provide illustrative examples of thermal performance data obtained when a heated back plate is used as compared to when a heated back plate is not used. For both figures the heated back plate comprise a 5 mm layer of fiberglass insulation positioned between the reaction vessel and an aluminum plate coupled to a kapton heating strip. For the data represented in FIG. 29A, the temperature of the aluminum plate was held at a substantially constant 94° C. and demonstrates a consistent temperature within the internal environment of reaction vessel 622 using multiple temperature sensors measuring from the "front" of the vessel (i.e. adjacent to the temperature control module) and the "back" of the vessel (i.e. adjacent to the temperature control module). It is notable that the consistent temperature is comfortably within the optimal temperature range for the denaturing step. This is in contrast to the data represented in FIG. 29B where the temperature at the back of the vessel fails to reach the optimal temperature range when the aluminum plate is at the ambient room temperature.

In some embodiments of device 600, components of reaction vessel 622, first liquid transfer channel 625, second liquid transfer channel 626, and third air vent channel 627 may be made of a soft resin. In some embodiments, reaction vessel 622 comprises a substantially planar device with a rigid frame that defines the outer perimeter of reaction vessel 622 and lateral walls comprising a thin film that is flexible and enables efficient thermal transfer to and from the interior compartment of reaction vessel 622. Embodiments of the rigid frame of reaction vessel 622 may include bar shaped element 629 positioned between first liquid transfer channel 625 and third air vent channel 627 that prevents collapsing of the thin film walls. In some embodiments, bar shaped element 629 may be tapered to get thinner towards the interior compartment defined by reaction vessel 622.

For example, the outer frame of reaction vessel 622 may be constructed of virgin polypropylene of about 1.6 mm in thickness that provides rigidity, defines an internal chamber between the thin film walls, prevents wrinkles that can form in the thin film walls that can impede fluid flow, and defines a downward slope of about 25 degrees towards second liquid transfer channel 626, relative to the force of gravity when installed for operation in an embodiment of device 100. The thin film walls may be heat sealed or laminated to the outer frame and also constructed of virgin polypropylene of about 0.4 mm in thickness that provides flexibility and efficient thermal transfer characteristics. In the present example, the combination of the slope provided by the rigid frame, flexible walls, and air vent channel enables efficient filling and draining of reaction vessel 522 where filling 17 ml of fluid takes about 2 minutes and draining takes about 3 minutes 45 seconds. Alternatively, a pump could perform or assist the draining which would have added benefits of reduces the machine height (because there is no longer a reliance on gravity) as well as enable back flushing fluid into and out of reaction vessel 622.

Accordingly, some embodiments of device 600 may be provided with frame 680 shown in FIG. 27 in order to hold nucleic acid amplification unit 620 and each liquid transfer channel as well as to provide heat insulating properties to reaction vessel 622. For example, frame 680 comprises a first holding part 680a which surrounds and holds the side surface of emulsion generation unit 610, a second holding part 680b which sandwiches and holds the outer frame of reaction vessel 622, and a third holding part 680c which surrounds and holds the side surface of emulsion breaking unit 630. As a result, it is possible to fix the positions of emulsion generation unit 610, reaction vessel 622, and emulsion breaking unit 640 and to hold the units at positions appropriate for transfer by means of gravity flow. A further benefit is also that emulsion generation unit 610, reaction vessel 622, and emulsion breaking unit 630 are operatively connected into a single unit that can be easily installed and detached from device 100 to improve usability and user interaction and may be provided as a combined disposable component.

Next, an overview of the processing of device 600 of Embodiment 4 is described. First, each solution and the like is loaded into emulsion generation unit 610 using a dispensing burette (not shown) of nozzle unit 1010, and the solution is stirred with the stirring rod 614 to generate an emulsion. The circuit opening and closing device 625a of first liquid transfer channel 625 is opened so as to transfer the emulsion by means of gravity flow from emulsion generation unit 610 to reaction vessel 622 via first liquid transfer channel 625. Nucleic acid amplification unit 120 amplifies the nucleic acids within reaction vessel 622 by executing a prescribed thermal cycle, as described above. The emulsion containing the amplified nucleic acids immobilized on beads is then transferred by means of gravity flow from reaction vessel 622 to emulsion breaking unit 630 via second liquid transfer channel 626 in a state in which the channel opening and closing device 626a is opened. By connecting the dispensing burette of nozzle unit 1010 to the opening end part 627b of third liquid transfer channel 627 and pressure-feeding water in a state in which channel opening and closing device 627a is opened, it is possible to promote the transfer of the solution containing the amplified nucleic acids by means of gravity flow from reaction vessel 622 to emulsion breaking unit 630. In emulsion breaking unit 630, after a breaking solution is added using the dispensing burette of nozzle unit 1010, the solution is stirred with the stirring rod 614 and the emulsion containing the amplified nucleic acids is broken. After breaking, the solution containing the amplified nucleic acids is transferred to a nucleic acid purification unit (not shown) using the dispensing burette of the nozzle unit 1010 and is purified.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

While this specification contains many specific implementation details, these should not be construed as limitations on the scope of any inventions or of what may be claimed, but rather as descriptions of features specific to particular embodiments of the systems and methods described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

What is claimed is:

1. A device for automatically executing a process of generating an emulsion containing nucleic acids, amplifying the nucleic acids in the emulsion, breaking the emulsion, and separating and purifying said amplified nucleic acids, said device comprising:
    an emulsion generation unit for sealing beads to which nucleic acids are bound in a water-in-oil type emulsion, wherein the emulsion generation unit comprises a container;
    a nucleic acid amplification unit provided with a reaction vessel for amplifying said nucleic acids and a heating and cooling part for heating and cooling the reaction vessel;
    an emulsion breaking unit for breaking the emulsion after nucleic acid amplification, wherein the emulsion breaking unit comprises a container and is connected to the reaction vessel by a channel; and
    a nucleic acid purification unit for recovering said amplified nucleic acids from said emulsion breaking unit, wherein the nucleic acid purification unit comprises multiple tubes,
    wherein a head drop is disposed between said nucleic acid amplification unit and said emulsion generation unit and/or between said emulsion breaking unit and said nucleic acid amplification unit via a plurality of liquid transfer channels for liquid transfer, and
    wherein.
    said nucleic acid amplification unit is disposed below said emulsion generation unit, and said emulsion breaking unit is disposed below said nucleic acid amplification unit.

2. The device of claim 1, wherein
    a channel opening and closing device is provided on said liquid transfer channels.

3. The device of claim 1, wherein
    said liquid transfer channels are formed from soft tubes, hoses, or films.

4. The device of claim 1, wherein
    said liquid transfer channels are molded integrally with or attached to at least one of said units.

5. The device of claim 1, wherein
    said reaction vessel comprises a bag.

6. The device of claim 1, wherein
    said nucleic acid amplification unit is covered by a heat-insulating material.

7. The device of claim 1 further comprising
    a fluid volume sensor for detecting the fluid volume inside at least one of said units.

8. The device of claim 1, further comprising
    a frame for holding at least one of said emulsion generation unit, said nucleic acid amplification unit, and said emulsion breaking unit.

9. The device of claim 1, further comprising
    an automatic processing mechanism for performing prescribed processing selected from the group consisting of dispensing, stirring, and suction processing of the emulsion or solution inside at least one of said emulsion generation unit, said nucleic acid amplification unit, said emulsion breaking unit, and said nucleic acid purification unit, wherein said automatic processing mechanism comprises a dispensing burette, a magnet for adsorbing a plurality of magnetic beads, a stirring instrument for stirring the contents of at least one of said units, a nozzle unit, or combinations thereof.

10. The device of claim 9, further comprising
    a moving mechanism for moving said automatic processing mechanism three-dimensionally.

11. The device of claim 10, wherein
    said moving mechanism moves said automatic processing mechanism to at least one of the positions of said emulsion generation unit, said nucleic acid amplification unit, said emulsion breaking unit, and said nucleic acid purification unit.

12. The device of claim 11, further comprising
    an operating stage on an upper surface of the device of claim 1; wherein said moving mechanism moves said automatic processing mechanism three-dimensionally on said operating stage.

13. The device of claim 10, wherein
    said moving mechanism comprises a first direction driving part for driving said automatic processing mechanism in a first direction, a second direction driving part for driving said automatic processing mechanism in a second direction differing from said first direction, and a third direction driving part for driving said automatic processing mechanism in a third direction differing from said first and second directions.

14. The device of claim 13, wherein
    said first direction of said first direction driving part is a direction inclined with respect to a horizontal plane.

15. A method for generating an emulsion containing nucleic acids, amplifying the nucleic acids in the emulsion, breaking the emulsion, and separating and purifying said amplified nucleic acids using the device of claim 1.

* * * * *